United States Patent [19]
Rangan

[11] Patent Number: 5,244,802
[45] Date of Patent: Sep. 14, 1993

[54] REGENERATION OF COTTON

[75] Inventor: Thirumale S. Rangan, Pasadena, Calif.

[73] Assignee: Phytogen, Pasadena, Calif.

[21] Appl. No.: 680,048

[22] Filed: Mar. 29, 1991

Related U.S. Application Data

[63] Continuation of Ser. No. 122,200, Nov. 18, 1987, abandoned.

[51] Int. Cl.$^5$ .......................... C12N 5/00; C12N 5/02
[52] U.S. Cl. .......................... 435/240.5; 435/240.46; 435/240.49; 435/240.54
[58] Field of Search ............ 435/240.49, 240.50, 435/240.54, 240.46

[56] References Cited

U.S. PATENT DOCUMENTS 4,672,035  6/1987  Davidonis et al. ................. 435/240

OTHER PUBLICATIONS

Price et al. (1984) in PV Ammirato et al., eds., Handbook of Plant Cell Culture, vol. 3, Macmillan Publishing Co., New York, pp. 499 and 503.
Trolinder, N. (1986) Dissertation Abstracts International 47(06): 2250B–2251B.
Davidonis et al. 1983, Plant Science Letters 32:89–93.
Price et al. 1979, Planta 145: 305–307.
Shoemaker et al. 1986, Plant Cell Reports 5: 178–181.
Finer et al. 1984, Plant Cell Reports 3: 41–43.
Mitten et al. 1985, Proc. Beltwide Cotton Production Research Conferences, Jan. 6, 1985–Jan. 11, 1985, New Orleans, La., pp. 57–58.
Rangan eta l. 1984, In Vitro 20:256.
Gawel et al. 1990, Euphytica 49: 249–253.
Trolinder et al. 1989, Plant Cell Reports 8: 133–136.
Umbeck et al. 1987, Bio/Technology 5(3): 263–266.
Smith et al. 1977, In Vitro 13(5): 329–334.
Davidonis and Hamilton, 1983–Plant Science Letters 32(1983) 89–93.
Donna H. Mitten—Somatic Embryogenesis in *Gossypium Hirsutum L.* 1985. Beltwide Cotton Prod. Res. Cont., New Orleans, La., pp. 57–58.
Nick J. Gawel—Somatic embryogenesis from leaf and petiole callus cultures. Plant Cell Reports 5(6): 457–459 (1986).
Ebrahim Firoozabady—Transformation of cotton (*Gossypium hirsutum L.*) by *Agrobacterium tumefaciens* and regeneration of transgenic palnts. 1987. Plant Mol. Biol. 10:105–116.
R. C. Shoemaker—Characterization of somatic embryogenesis and plant regeneration in cotton (*Gossypium hirsutum L.*) 1986 Plant Cell Reports 5(3): 178–181.
Rangan, Zavala & IP—In vitro 20:256 1984.

*Primary Examiner*—David T. Fox
*Attorney, Agent, or Firm*—Christie, Parker & Hale

[57] ABSTRACT

There are provided methods for regenerating cotton by tissue and suspension culture starting with explants which are the hypocotyl, cotyledon or immature embryos. This also taught methods to transform cotton and improve cotton by selective growth.

48 Claims, 29 Drawing Sheets

16  16

REGENERATION OF COTTON

CROSS-REFERENCE TO RELATED APPLICATIONS

This is a continuation of application Ser. No. 07/122,200, filed Nov. 18, 1987, now abandoned.

BACKGROUND OF THE INVENTION

This invention is directed to plant regeneration and transformation of cotton, particularly cotton of the species *Gossypium hirsutum L.*

In recent years many tissues of diverse origin from plants belonging to different taxonomic groups have been established as in vitro tissue culture. Some of the factors controlling growth and differentiation of such cultures have also been determined. The establishment of subtle interactions among the different groups of plant hormones, and plant growth regulators, operating either directly or indirectly, alone or in synergistic combination, have given to some degree an insight into certain interrelationships that may exist among cells, tissues and organs. The information is, however, by no means complete.

For some time it has been known that plant cell cultures can be maintained in a nondifferentiating proliferative state indefinitely. It has, however, only been recently found that redifferentiation of tissues, organs or whole plant organisms can be experimentally induced. Since the demonstrations by Skoog et al "Chemical regulation of growth and organ formation in plant tissues cultured in vitro," *Symp. Soc. Exp. Biol.* 11:18-130, 1958, incorporated herein by reference, that the relative ratio of a cytokinin to an auxin determines the nature of organogenesis in tobacco pith tissue. Reorganization or regeneration from callus cultures includes the formation of shoot primordia or embryos, both of which ultimately lead to plantlet development in vitro.

The tendency for organogenesis vs. embryogenesis still depends upon the species involved and the presence of certain triggering factors which are chemical and/or physical in nature.

In 1902, Haberlandt "Kulturversuche mit isolierten pflanzenzellen," *Mat. Kl. Kais, Akad, Wiss. Wien* 111:62, incorporated herein by reference, postulated that plant cells possessed the ability to produce entire plants and predicted that this would someday be demonstrable in cell cultures. In 1965, Reinert "Untersuchungen uber die morphogenese an Gewebekulturen," *Ber. dt. Bot. Ges.* 71:15, and Steward et al, "Growth and organized development of cultured cells/II. Organization in cultures grown from freely suspended cells," *Am. Bot.* 45:705-708, working independently, confirmed the occurrence of in vitro somatic embryogenesis. Both references are incorporated herein by reference. In experimentally manipulating somatic embryogenesis, it is believed that two components of the culture media, an auxin and the nitrogen source, play crucial roles.

It has also been shown that the process of somatic embryogenesis takes place in two stages: first, the induction of cells with embryogenic competence in the presence of a high concentration of auxin; and second, the development of embryonic cell masses into embryos in the absence of or at a low concentration of auxin.

The induction of organogenesis or embryogenesis leads to distinct structural patterns in the callus. Detailed study of several plant species has enabled certain generalizations to be made about the developmental pathways leading to shoot, bud or embryo development.

The application of tissue culture techniques to the regeneration of plants via organogenesis or embryogenesis remains perhaps the most important contribution of basic studies in morphogenesis to commercial application.

Beasley reported the formation of callus in ovule cultures of cotton in 1971, "In vitro culture of fertilized cotton ovules," *Bioscience* 21:906:907, 1971, incorporated herein by reference. Later, Hsu et al "Callus induction by (2-chlorethyl) phosphonic acid (CPA) in cultured cotton ovules," *Physiol. Plant* 36:150-153, 1976, incorporated herein by reference, observed a stimulation of growth of callus obtained from ovules due to the addition of CPA and gibberellic acid to the medium. Callus cultures from other explants such as (a) leaf Davis et al., "In vitro culture of callus tissues and cell suspensions from okra (*Hibiscus esculentus*) and cotton (*Gossypium hirsutum*)," *In vitro* 9:395-398, 1974, both incorporated herein by reference; (b) hypocotyl, Schenk et al., "Medium and technique for induction and growth of monocotyledonous and dicotyledonous plant cell cultures," *Can. J. Bot.* 50:199-204, 1972, incorporated herein by reference and (c) cotyledons Rani et al., "Establishment of Tissue Cultures of Cotton," *Plant Sci. Lett.* 7:163-169, 1976, incorporated herein by reference) have been established for *Gossypium hirsutum* and *G. arboreum.*

Katterman et al, "The influence of a strong reducing agent upon initiation of callus from the germinating seedlings of *Gossypium barbadense,* " *Physiol. Plant* 40:98-101, 1977, incorporated herein by reference, observed that the compact callus from cotyledons of *G. barbadense* formed roots, and in one instance regeneration of a complete plant was also obtained. Smith et al., "Defined conditions for the initiation and growth of cotton callus in vitro. *Gossypium arboreum*," In vitro 13:329-334, 1977, incorporated herein by reference, determined conditions for initiation and subculture of hypocotyl-derived callus of *G. arboreum*. Subsequently, Price et al., "Callus cultures of six species of cotton (*Gossypium L*) on defined media," Pl *Sci. Lett.* 8:115-119, 1977, and "Tissue culture of Gossypium species and its potential in cotton genetics and crop improvement," *Beltwide Cotton Production Research Conference Proc.* pp. 51-55, 1977, of the National Cotton Council, Memphis, each incorporated herein by reference, defined conditions for the initiation and subculture of callus from five species of Gossypium.

One of the common problems in establishing cultures of many plant species is the "browning" of the explant in the culture medium. In cotton, this leaching of polyphenols was overcome by replacing sucrose with glucose, and by transferring the cultures to a fresh medium every 10 days. After 3 or 4 passages on glucose supplemented medium, the browning completely disappeared and the cultures could be transferred back to sucrose-supplemented media. Although difficulties with the induction, browning and maintenance of callus during subcultures have been overcome with certain Gossypium species, all attempts to regenerate plants from callus cultures have been either unsuccessful or have involved several time-consuming steps. Davidonis and Hamilton "Plant Regeneration from Callus Tissue of *Gossypium hirsutum,*" L. *Plant Sci. Lett.* 32:89-93, 1983, incorporated herein by reference, reported the eventual formation of embryos two years after the initiation of culture.

Although many growth substances, such as natural phytohormones and synthetic growth regulating compounds have been utilized in tissue culture media to bring about plant regeneration in vitro, no generalization, much less specifics, of the effects of different substances on plant regeneration has been arrived at. Indeed, the same substances, when applied to different plant species, may either inhibit growth, enhance growth, or have no effect whatsoever. Therefore, aside from certain standard procedures, it remains necessarily a difficult task to arrive at a working protocol for plant regeneration for any new species and by many orders of magnitude a more difficult task to achieve plant transformation.

The present invention provides a method for the rapid regeneration of cotton plants from segments excised from seedlings or from unmature zygotic embryos. The method described offers a high degree of repeatability and reliability and it enables genetic transformation of cotton plants.

SUMMARY OF THE INVENTION

There are provided methods for the regeneration, with optional transformation, of a cotton plant from somatic cells.

Seed is sterilized and grown in the dark to a seedling. The seedling is one source of an explant, usually the hypocotyl and the cotyledon. Another source is the immature zygotic embryo from the developing fruit. The explant is subdivided and cultured on a first callus growth medium (containing glucose) for a period of time to allow a callus to develop from the explant on a culture medium which copes with phenolic secretions and stimulates cells of the explant to divide and proliferate. The callus, after passing through the phenolic secretion stage, is transferred to a fresh callus growth medium (containing sucrose) which develops the callus to an embryogenic callus. The embryo may then be subcultured to produce more embryogenic callus or transferred to another growth medium (plant germination medium) and cultured for a period of time sufficient to develop a plantlet which after another period of growth is transferred to a greenhouse, then into the field and grown to a mature plant from which seeds can be harvested.

The embryogenic callus may also be cultured in suspension. In this procedure, after the period of growth, the suspension containing embryogenic clumps greater than about 600 microns, preferably greater than about 800 microns in size, are isolated and utilized for plant production. Suspensions containing embryogenic clumps are recycled to the callus growth medium for growth to plant forming callus or maintained as an embryo source.

Transformation may occur at the explant, callus or suspension development stage. Transformation involves exposing the explant, callus and/or embryogenic callus to the action of an Agrobacterium vector containing an expressible gene sequence foreign to cotton for a time sufficient for the gene to be transferred into the cells. The residual Agrobacterium is then killed off with an antibiotic which is toxic to the Agrobacterium. This is followed by selection of the transformed cells and/or embryogenic callus for development into transformed plantlets. In suspension culture, transformation and/or selection can occur prior to, or following, separation of embryogenic callus from cells and callus too immature to be embryogenic.

Plants of unique phenotypic traits are obtainable, and there are provided new cotton plants which have resistance to antibotics normally inhibitory to plant cell growth; cotton plants which have increased resistance or tolerance to herbicides, fungal pathogens and cotton plants which exhibit better yield and improved fiber quality.

BRIEF DESCRIPTION OF THE DRAWINGS

FIG. 10 shows somatic embryos developing from the selected antibiotic resistance cells of FIG. 9 on an antibiotic-supplemented medium.

FIG. 11 shows germinating embryos of transformed somatic embryos containing a gene conferring resistance to the herbicide glyphosate.

FIG. 12 shows cotton plantlets developed from the embryos of FIG. 11.

FIG. 13 shows germinating somatic embryos transformed to confer resistance to Lepidopterous insects with leaf 14 and root 16 development.

FIG. 14 shows plantlets developed from the embryos of FIG. 13.

FIG. 15 shows a plantlet of the variety Siokra developed from transformed embryos exhibiting a resistance to kanamycin.

DETAILED DESCRIPTION

Figure 1:
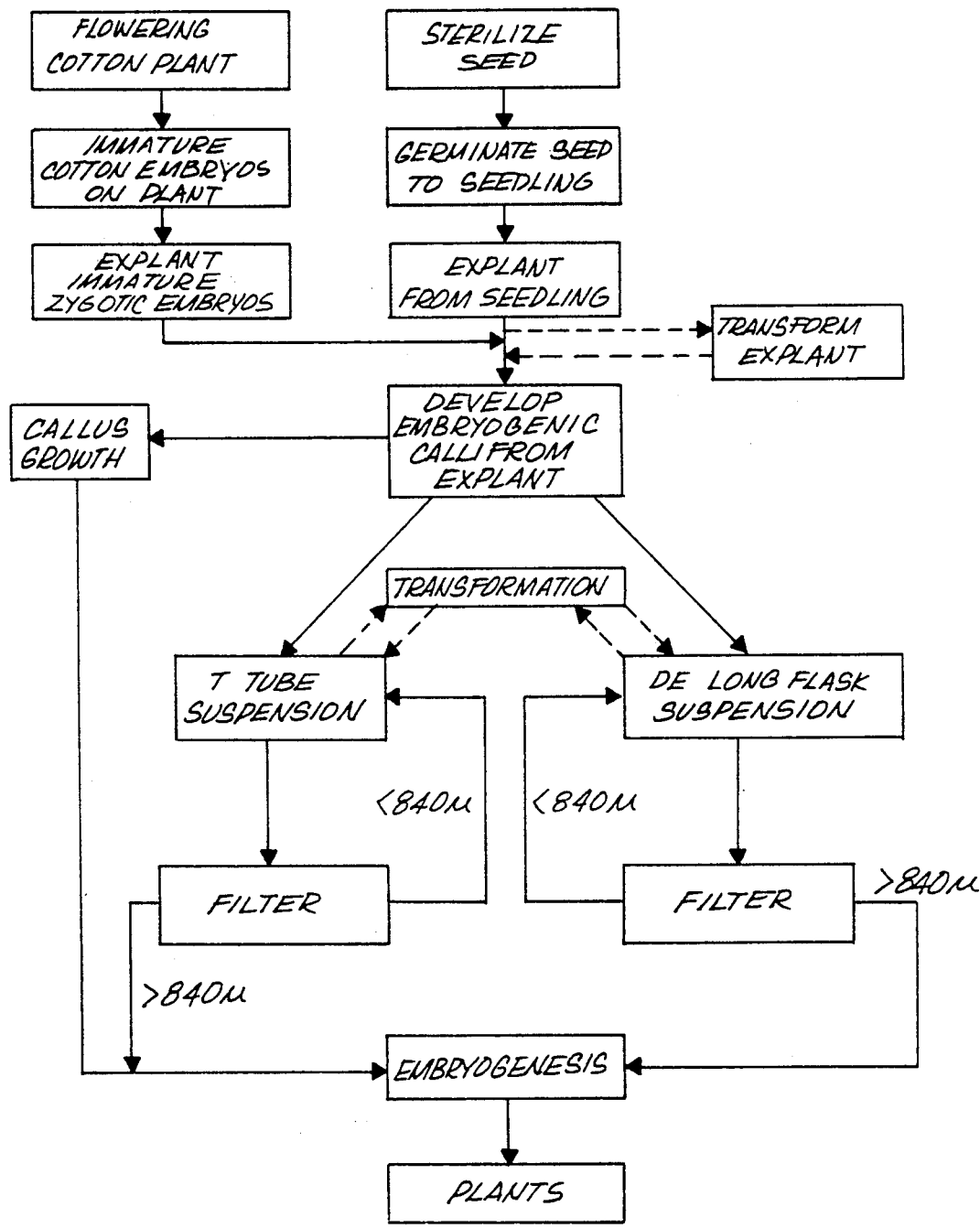
FIG. 1 presents, diagramatically, preferred procedures for development of cotton plants from seed by tissue culture techniques with a showing of establishing zones of transformation.

The present invention is directed to the regeneration by tissue culture of cotton plants, particularly plants of the genus *Gossypium hirsutum*, from somatic cells, for propagation in the field. Optionally, the cells may be transformed to include foreign genetic information.

The various growth media useful in accordance with this invention are as follows:

SEED GERMINATION GROWTH MEDIUM
COMPOSITION OF MODIFIED WHITE'S STOCK SOLUTION
(Phytomorphology 11:109–127, 1961 incorporated herein by reference)

| Component | Concentration per 1000 ml. | Comments |
|---|---|---|
| $MgSO_4 \cdot 7 H_2O$ | 3.6 g | Dissolve and make up |
| $Na_2SO_4$ | 2.0 g | the final volume to |
| $NaH_2PO_4 \cdot H_2O$ | 1.65 g | 1000 ml. Label White's A Stock. Use 100 ml/l of final medium. |
| $Ca(NO_3)_2 \cdot 4 H_2O$ | 2.6 g | Dissolve and make up |
| $KNO_3$ | 800 mg | the final volume to |
| $KCl$ | 650 mg | 1000 ml. Label White's B Stock. Use 100 ml/l of final medium. |
| $Na_2MoO_4 \cdot 2H_2O$ | 2.5 mg | Dissolve and make up |
| $CoCl_2 \cdot 6H_2O$ | 2.5 mg | the final volume to |
| $MnSO_4 \cdot H_2O$ | 300 mg | 100 ml. Label White's |
| $ZnSO_4 \cdot 7 H_2O$ | 50 mg | C Stock. Use 1.0 ml/l |
| $CuSO_4 \cdot 5 H_2O$ | 2.5 mg | of final medium. |
| $H_3BO_3$ | 50 mg | |
| Fe EDTA | | Use 10 ml/l of MSFe EDTA. |
| Organic | | Use 10 ml/l of MS organic. |

CALLUS GROWTH/MAINTENANCE MEDIUM
COMPOSITION OF MURASHIGE & SKOOG (MS) STOCK SOLUTIONS
(Physiol. Plant 15:473–497, 1962 incorporated herein by reference)

| Component | Concentration per 1000 ml. of Stock | Comments |
|---|---|---|
| $NH_4NO_3$ | 41.26 g | Dissolve and make up the |
| $KNO_3$ | 47.50 g | final volume to 1000 |
| $CaCl_2 \cdot 2 H_2O$ | 11.00 g | ml. Use 40 ml/l of final |
| $MgSO_4 \cdot 7 H_2O$ | 9.25 g | medium. |
| $KH_2PO_4$ | 4.25 g | |
| KI | 83 mg | Dissolve and make up |
| $H_3BO_3$ | 620 mg | the final volume to |
| $MnSO_4 \cdot H_2O$ | 1690 mg | 1000 ml. Label MS - |
| $ZnSo_4 \cdot 7 H_2O$ | 860 mg | Minor. Use 10 ml/l of |
| $Na_2MoO_4 \cdot 2 H_2O$ | 25 mg | final medium. |
| $CuSO_4 \cdot 5 H_2O$ | 2.5 mg | |
| $CoCl_2 \cdot 6 H_2O$ | 2.5 mg | |
| Nicotinic acid | 50 mg | Dissolve and make up |
| Pyridoxin HCl | 50 mg | the final volume to |
| Thiamine HCl | 10 mg | 1000 ml. Label MS - Organic. Freeze in 10 ml aliquots. Use 10 ml/l of final medium. |
| Fe EDTA | 2.78 g | Dissolve 2.78 g of |
| Fe $SO_4 \cdot 7H_2O$ | 3.73 g | $FeSO_4 \cdot 7 H_2O$ in about |
| $Na_2$ EDTA.2 $H_2O$ | | 200 ml of deionized water. Dissolve 3.73 g of $Na_2$ EDTA.2 $H_2O$ (disodium salt of ethylenediaminotetraacetic acid dihydrate) in 200 ml of deionized water in another beaker. Heat the $Na_2$ EDTA solution on a hot plate for about 10 minutes. While constantly stirring, add $FeSO_4$ solution to $Na_2$ EDTA solution. Cool the solution to room temperature and make up the volume to 1000 ml. Label MS EDTA. Cover bottle with foil and store in refrigerator. Use 10 ml/l of final medium. |
| Thiamine HCl | 50 mg | Dissolve and make up the volume to 500 ml. Label MS - Thiamine. Use 4.0 ml/l of final medium. As if required. |
| Inositol | 10 g | Dissolve and make up |
| Glycine | 0.2 g | the final volume to 1000 ml. Label MS - glycine/inositol. Use 10 ml/l of final medium. |

EMBRYO GERMINATION MEDIUM
COMPOSITION OF BEASLEY AND TING'S STOCK SOLUTIONS
(Am. J. Bot. 60:130–139, 1973 incorporated herein by reference)

| Component | Concentration per 1000 ml. | Comments |
|---|---|---|
| $KH_2PO_4$ | 2.72 g | Dissolve and make up |
| $H_3BO_3$ | 61.83 mg | the volume to 100 ml. |
| $Na_2MoO4.2 H_2O$ | 2.42 mg | Label B&T - A Stock. Use 10 ml/l of final medium. |
| $CaCl_2 \cdot 2 H_2O$ | 4.41 g | Dissolve and make up |
| KI | 8.3 mg | the volume to 100 ml. |
| $CoCl_2 \cdot 6 H_2O$ | 0.24 mg | Label B&T - B Stock. Use 10 ml/l of final medium. |
| $MgSO_4 \cdot 7 H_2O$ | 4.93 g | Dissolve and make up |
| $MnSO_4 \cdot H_2O$ | 169.02 mg | the volume to 100 ml. |
| $ZnSO_4 \cdot 7 H_2O$ | 86.27 mg | Label B&T - C Stock. |
| $CuSO_4 \cdot 5 H_2O$ | 0.25 mg | Use 10 ml/l of final medium. |
| $KNO_3$ | 25.275 g | Dissolve and make up the volume to 200 ml. Label B&T - D Stock. Use 40 ml/l of final medium. |
| Nicotinic acid | 4.92 mg | Dissolve and make up |
| Pyridoxin HCL | 8.22 mg | the final volume to |
| Thiamine HCL | 13.49 mg | 100 ml. Label B&T - Organics. Use 10 ml/l of final medium. |
| Fe EDTA | | Use 10 ml/l of MS Fe |

-continued

| | EDTA. |
|---|---|
| Inositol | 100 mg/l of final medium. |
| NH$_4$NO$_3$ (15 uM) | 1200.6 mg/l of final medium. |

With any of the above solutions, the following procedure is used to prepare one liter of the medium. There is provided as a base, 200 ml of deionized water and the various stock solutions are added in the amounts stated for 1 liter. For example, if there is to be employed 10 ml of a stock in the final medium, then 10 ml of the stock are added to the 200 ml of the distilled water. To ensure the salts stay in solution, stock solutions are normally added in the order shown in the formulations above. After thoroughly mixing, additional deionized water is added to the mixture to bring it to, as required 500 ml, and the mixture adjusted in pH to a value of from about 5.8 to 6.0. The final volume is brought to 1,000 ml and there is normally added tissue culture Agar, or its equivalent, to a level of about 0.8% by weight. This is to provide some solidity to the solution to reduce flow. The mixture is then autoclaved for about 5 to 20 minutes at a pressure of 15-21 lbs/in$^2$ to kill any contaminating organism, and suitably labeled and stored as a sterile medium.

Briefly, cotton seeds are sterilized and germinated on a suitable seed germination medium, such as a basal agar medium, in the dark for a time sufficient to produce seedlings. The normal period of growth is up to about 4 weeks, typically 7 to 14 days.

Segments of explants are excised from the seedling. It is preferred that the explant come from the hypocotyl or cotyledon. In the alternative, one can equally use immature embryos obtained from the developing fruits of greenhouse or field grown cotton plants as the explant. The explant segments are cultured on a suitable first callus growth medium, preferably a or full Murashige and Skoog (MS) nutrient medium containing glucose. Growth occurs by culturing at a temperature of from about 25° to about 35° C. in a light/dark cycle of about 16 hours of light and about 8 hours of dark. Culturing is the procedure whereby the medium is replaced at periodic intervals as the nutrients are consumed and continued for approximately about 3 to about 4 weeks, or until undifferentiated callus is formed and phenolics are no longer produced. The callus is transferred to a second callus growth medium, preferably an MS medium supplemented with naphthaleneacetic acid (NAA) and sucrose as the carbon source and cultured for three to four months to produce embryos.

The embryos may are then maintained in the second callus growth medium to maintain an embryo supply or transferred to a plant germination medium such as Beasley and Ting's medium, preferably containing casein hydrolysate and source of ammonium, cultured for 2 to 3 months to produce plantlets.

The plantlets are transferred to soil under high humidity conditions, then transplanted to larger pots in a greenhouse and finally transferred to the field for growth to maturity.

The methods briefly described herein have been successfully employed to induce somatic embryo formation in cotton of the species Gossypium hirsutum by tissue and suspension cultures and, ultimately, to obtain mature plants from hypocotyl and cotyledon derived callus cultures of Acala varieties of Gossypium hirsutum including SJ2, SJ4, SJ5, B1644, B1810, B2724, GC510 and C1 and non Acala "picker" Siokra and "stripper" variety FC 2017. Cultures have been transformed to normal plants with novel traits or properties.

More particularly, the procedure involves first the sterilizing of the cotton seeds. Suitable sterilization may be achieved by immersing the seeds in 95% ethanol for 2 to 3 minutes, rinsing in sterile water one or more times, then soaking the seeds in a 15% solution of sodium hypochlorite for 15 to 20 minutes, and rinsing several times with sterile water.

The sterilized seeds are then transferred to a first medium, termed a seed germination medium. A seed germination medium is one of normal salt content. A suitable germination medium is a basal agar medium, including White's medium or half-strength MS medium (One-half ingredient strength). Germination normally occurs in the dark over an about 12 to about 14 day period.

Hypocotyl and/or cotyledons are preferably excised from the germinated seed, subdivided or cut into segments, and cultured on a first callus growth medium such as an MS medium supplemented with growth substances. The presently preferred medium is the MS medium supplemented with about 0.4 mg/l thiamine hydrochloride, about 30 g/l glucose, about 2 mg/l naphthaleneacetic acid, about 1 mg/l kinetin, a common growth regulator, and about 100 mg/l inositol and agar. Thiamine hydrochloride can generally range in concentration from 0.1 to about 0.5 mg/l, glucose about 20 to about, 30 g/l, about 1 to about 10 mg/l naphthaleneacetic acid, about 1 to about 2 mg/l kinetin and about 50 to about 100 mg/l inositol.

The cultures are maintained at a temperature of about 25° to about 35° C., preferably about 30° C. and with a light/dark cycle of about 16 hours of light and about 8 hours of dark. It is preferred to have a light intensity of about 2000 to 4000 lux, more preferably about 3000 to 4000 lux.

The callus formed is periodically subcultured at 3 to 4 week intervals and transferred to a fresh first callus growth medium. In the culturing of the explants, secretions of phenolic compounds from the explants can occur as evidenced by darkening of the cultured medium. In this instance, the medium is changed more regularly. Darkening has been avoided by changing the culture medium every 10 days. Normally, after three to five medium changes, phenolic secretions will disappear. When this occurs, the first callus growth medium can be replaced by fresh callus growth medium containing sucrose or supplemented with sucrose as a carbon source.

After 3 to 4 weeks of culture, for callus develops on the cut surfaces of the explants. The callus is then transferred to a fresh second callus growth maintenance medium which is preferably an MS medium combined with about 1 to about 10 mg/l, preferably about 1 to about 5 mg/l NAA. Cytokinin is employed at a concentration of from 0 to about 1 g/l. A callus growth medium is characterized as a high salt content medium containing as much as 10 times more salt than the seed germination medium. The essential difference between first and second callus growth medium is the carbon source. Glucose is used during period of phenolic secretions. Sucrose is used when secretion have stopped. The balance of the callus growth medium can remain the same or changed.

The callus is transferred of regular intervals to a fresh callus growth medium and, after generally about 5 to 7 passages or until an anthocyanin pigmentation becomes evident in a portion of the callus, which is followed by development of a yellowish-white embryogenic callus.

The embryogenic callus is then selectively subcultured and maintained by regular subculturing. The embryogenic callus contains somatic embryos at various stages of development. Some may have reached the point of development that enables growth into small plantlets. Most, however, require further development. Some may be advanced to germination. Other may be maintained as a source of embryos for future use.

Figure 2:
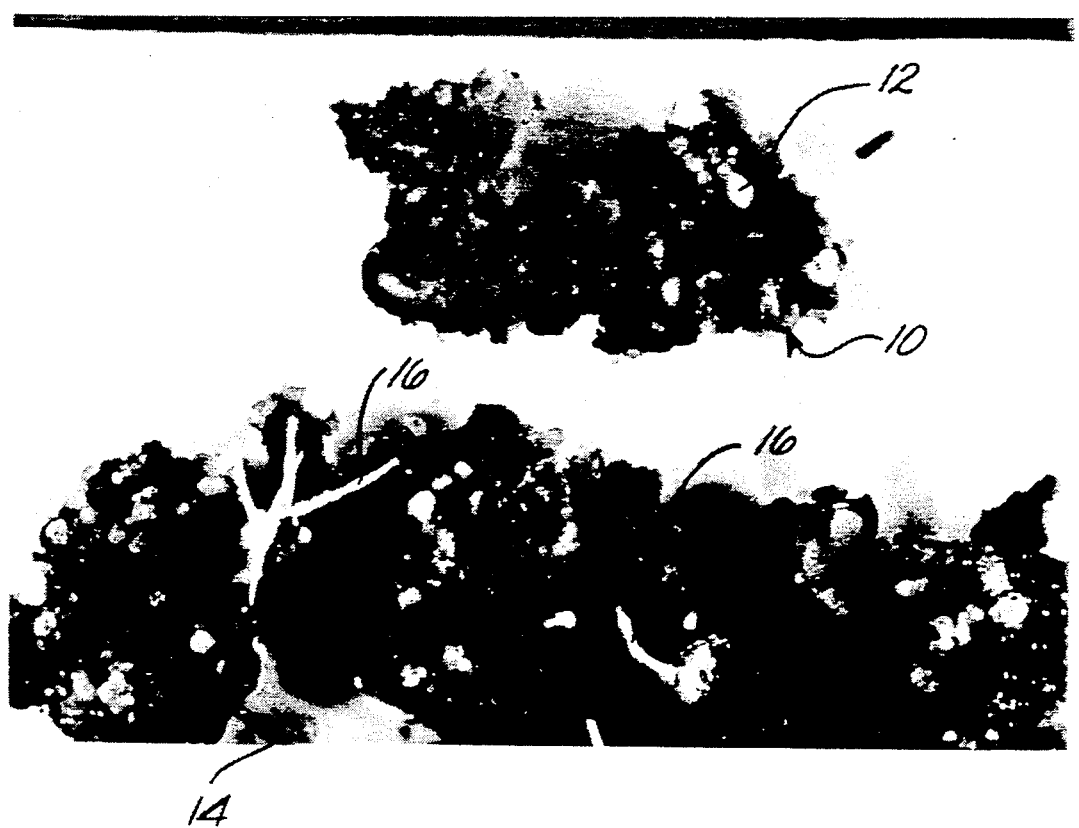
FIG. 2 is a photo illustration of embryogenic callus (10) of cotton with somatic embryos (12) at various stages of development including leaf (14) and root (16).
Figure 3:
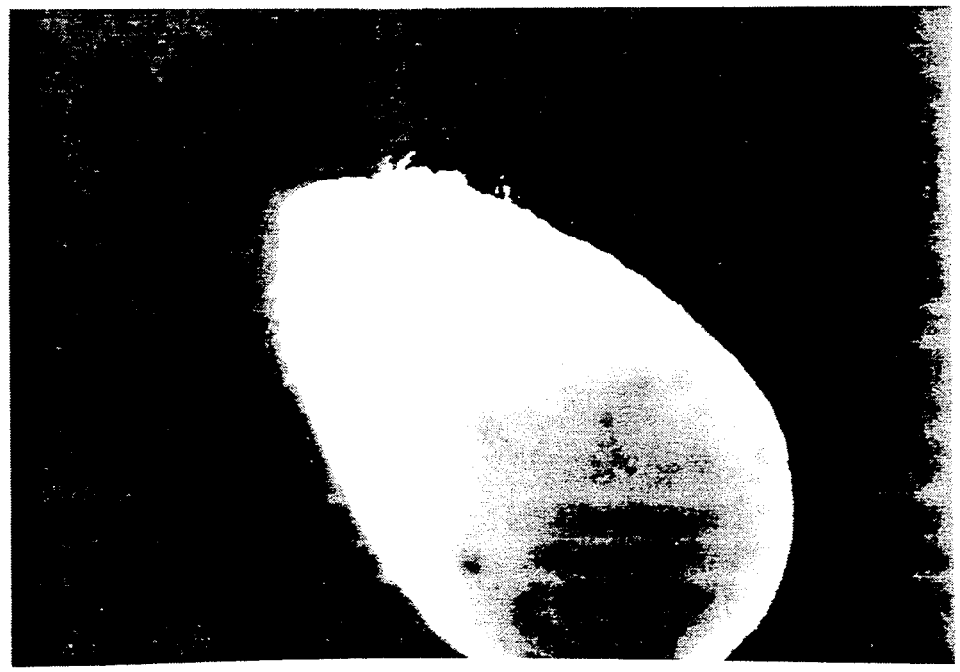
FIG. 3 is a photo illustration of a somatic cotton embryo at a late globular stage isolated to form the embryogenic callus culture as depicted in FIG. 2.

With reference to FIG. 2, there is illustrated this stage of development showing callus of Acala cotton 10 with somatic embryos 12 of differing size with some having emerging leaves 14 and roots 16. FIG. 3 illustrates a somatic embryo isolated at a late globular stage.

Figure 4:
FIG. 4, as with reference to FIG. 2, is a photo illustration of embryos and young plantlets (18) of cotton developing on an embryo germination medium.

With reference to FIG. 4, further development may be achieved by transferring the somatic embryos to a third growth medium, termed herein an embryo germination medium, which is a medium rich in nitrogen, usually in the form of ammonia or its equivalent. Suitable media include Beasley and Ting's medium, preferably supplemented with up to about 500 mg/l casein hydrolysate.

Germination occurs from somatic embryos and, within 2 to 3 months, a well developed plantlet 18 of up to 6 leaves and good root system is generally formed.

Figure 7:
FIG. 7 illustrates germinating embryos obtained from suspension cultures showing emerging leaves (14) and roots (16).
Figure 8:
FIG. 8 illustrates the development of plantlets of cotton growing on the embryo germination medium.

At this stage, the plantlets are transferred to soil in small clumps and grown in a standard incubator under conditions of high humidity. Temperature is normally maintained at about 25° to 30° C. (See FIG. 7).

After a period of growth, the small plants are transferred to larger pots in a greenhouse and thereafter transferred to field and grown to maturity. All the regenerated plants are preferably self-pollinated either while growing in the green house or in field conditions and the seeds collected. Seeds are then germinated and 4 to 5 week old seedlings transferred to the field for progeny row trials and other standard plant breeding procedures. Practicing the above procedure produces viable cotton plants from about 35% of the explants in the period of time from about 6 to about 8 months.

Proliferation of Embryogenic Cotton Cells In Suspension Cultures

As an alternative to allowing the growing embryogenic calli to be developed into a plant, the callus may be cut into smaller pieces and further developed using suspension culture techniques.

In this procedure, the suspension concentration is normally from about 750 to 1000 mg of callus parts to 8 ml. callus growth medium such as the second callus growth medium (MS medium supplemented with NAA), and allowed to grow in suspension. In a preferred embodiment, the suspension of the callus is inserted in T-tubes and placed on a roller drum rotating at about 1.5 rpm under a light regime of about 16 hours of light and about 8 hours of dark. Growth is for about 3 to 4 weeks.

Figure 5:
FIG. 5 is a photo illustration of small clumps of embryogenic cells from suspension cultures of cotton.
Figure 6:
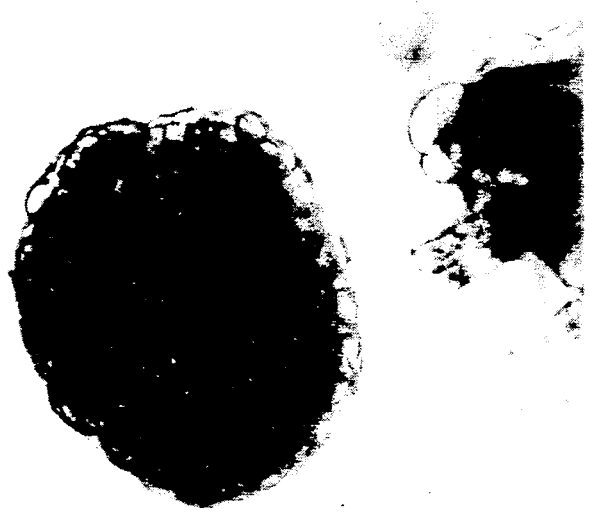
FIG. 6 is a photo illustration of a globular stage embryo from a suspension culture.

After about every 3 to 4 weeks, the suspension is filtered to remove large cell clumps of embryogenic callus depicted in groups in FIG. 5 and as isolated at late globular stages as shown in FIG. 6. The filtrate is returned to a nutrient medium for a 3 to 4 week period of growth. This procedure is repeated over and over with harvesting of large clumps at about 3 to 4 week intervals, at which time the medium is supplanted in whole or in part with fresh callus growth medium. Preferably, about 4 volumes or more of the fresh medium are added to about one volume of residual suspension. It is presently preferred that the filter employed have a mesh size greater than about 600 microns, preferably greater than 800 microns, as it has been observed the cell masses of a particle size less than 600 microns will not develop into plants, whereas cell masses greater than 600 microns and preferably greater than 800 microns have undergone sufficient differentiation so as to become embryogenic and capable of developing into viable plants.

Suspension cultures can also be initiated by transferring the embryogenic callus to a flask, such as a De-Long medium in an amount of about 20 ml of MS and NAA at a concentration of 2.0 mg/l. The flask is placed on a gyrotory shaker and is shaken at about 100-110 strokes per minute. After 3 to 4 weeks the suspension is suitable for filtration as described above to remove the large cell clumps for plant development.

More typically, after the third or fourth subculture, the cell suspension from the "T" tube or De Long or Erlenmeyer flask is plated onto agar-solidified MS medium containing NAA (2.0 mg/l) or Beasley & Ting's medium containing casein hydrolysate (500 mg/l) media and a source of nitrogen. Within 3-4 weeks embryogenic calli with developing embryos become visible. Likewise, the larger cell clumps when plated on the above media give rise to embryogenic clumps with developing embryos.

In both suspension growth methods, the MS media is used to promote and/or sustain embryos whereas the germination medium is employed for rapid plant development.

The seedling explants, if desired, can be transformed. In this procedure, cotyledon and/or hypocotyl segments of the sterilized seed can be used. Cotyledons are preferred.

The segments are placed in a medium containing an Agrobacterium vector containing a code (genetic marker) such as resistance to an antibiotic, such as for instance kanamycin, for a time sufficient for the vector to transfer the gene to the cells of the explant. Generally, contact times ranging from 1 minute to 24 hours may be used and may be accompanied with intermittent or gentle agitation. The explants are then removed and placed on agar-solidified callus growth medium such as a MS medium supplemented with NAA (2 mg/l) and incubated about 15 to 200 hours at 25° to 35° C., preferably 30° C., on a 16:8 hour light: dark regime.

After incubation, the explants are transferred to the same medium supplemented with the antibiotic cefotaxime, preferably in a concentration of 200 mg/l. Cefotaxime is included to prevent any remaining Agrobacterium from proliferating and overgrowing the plant tissues. Alternatively, the explants can be rinsed with MS medium supplemented with NAA (2mg/l) and incubated an additional 4 to 28 days before rinsing, then incubating the same medium containing cefotaxime. At the end of 4-5 weeks of culture on fresh medium, the developing callus, i.e., primary callus, is separated from the remainder of the primary explant tissue and transferred to MS medium containing NAA (2 mg/l), cefotaxime (200 mg/l) and an antibiotic such as kanamycin sulfate (50 mg/l). Transformed primary callus, identified by virtue of its ability to grow in the presence of the antibiotic (kanamycin), is selected and embryos developed, germinated and plants obtained following the procedure set forth above.

It is also feasible to achieve transformation of a cell suspension. Following a normal subculture growth cycle of 7 to 14 days, usually 7 to 10 days, cells are allowed to settle leaving a supernatant which is removed. The remaining concentrated suspended cells may be centrifuged at 4000×g for 5 minutes and the excess medium is discarded. The concentrated suspension cultures are resuspended in the 8 ml of the same medium which contains the Aqrobacterium. The suspension is transferred to "T" tubes and suitably agitated for incubation.

Following about 2 to 24 hours, preferably 3 to 5 hours, of incubation to allow for bacterial attachment and DNA transfer, the suspension is removed and allowed to settle. The supernatant containing the bacteria is discarded and the cells are washed with fresh medium. The suspension may, if desired, be centrifuged for about 5 minutes and the supernatant removed. In either event, the cells are resuspended in the same medium and transferred to a "T" tube or flask and suspension subculture resumed. The object is to minimize the amount of unattached Agrobacterium vector left in the cell suspension.

After about 15 to about 200 hours, typically 15 to about 72 hours, preferably 18 to 20 hours, the suspension is filtered to remove large clumps and washed with fresh liquid medium and allowed to settle. The suspension is resuspended in the fresh liquid medium containing cefotaxime (200 mg/l) and plated on a solidified medium in Petri dishes.

Alternatively, the suspension may be resuspended in fresh medium containing cefotaxime and allowed to grow an additional 4 to 28 days prior plating on solidified medium in Petri dishes. Cell concentration is 1 vol. of suspension cells plus 3 vol. of medium with cefotaxime. Kanamycin at 10 to 300 mg/l preferably about 20 to 200 mg/l more preferably about 40 to 80 mg/l is included in the medium for selection of transformed cells expressing the neomycin phosphotransferase (NPT) gene. Cells and embryos proliferating in the selective concentration of kanamycin are further grown as set forth above to mature somatic embryos capable of germinating and regenerating into whole plants according to the procedures described herein.

Figure 9:
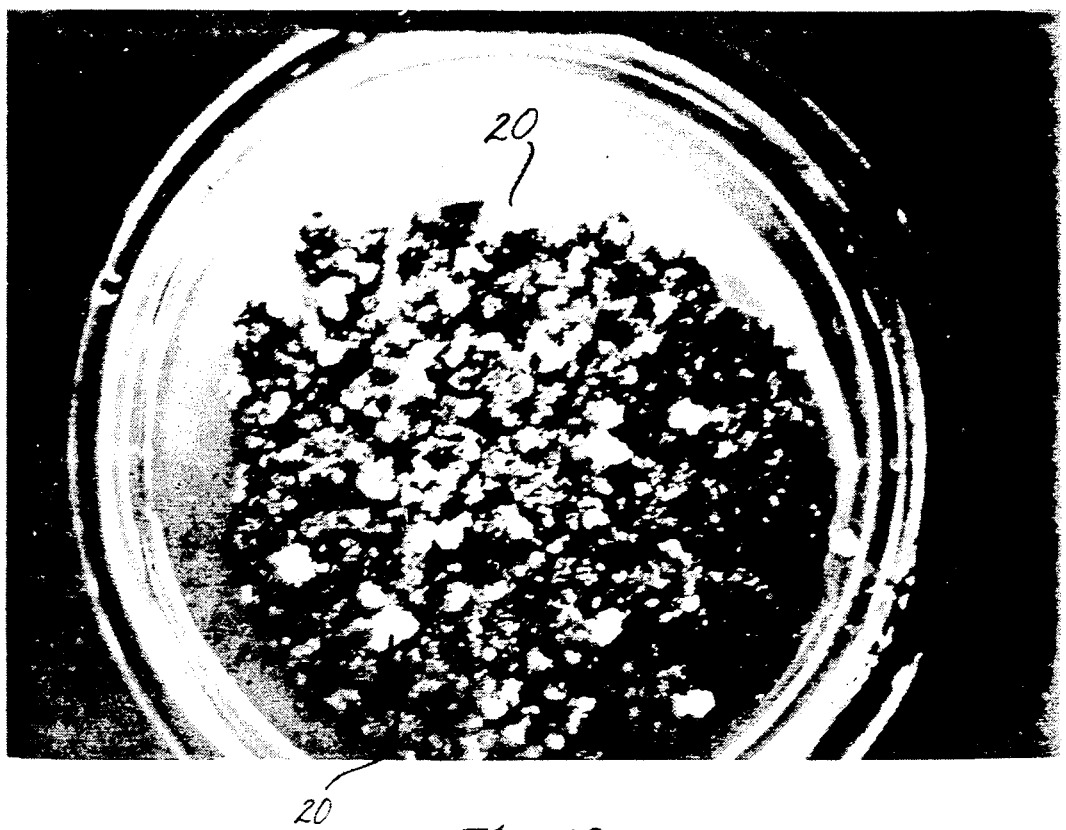
FIGS. 9 to 15 depict the genetic transformation of cotton, with FIG. 9 showing the development of cell colonies (20) from transformed cotton cells containing a gene for kanamycin resistance.
Figure 10:
Figure 11:
Figure 12:
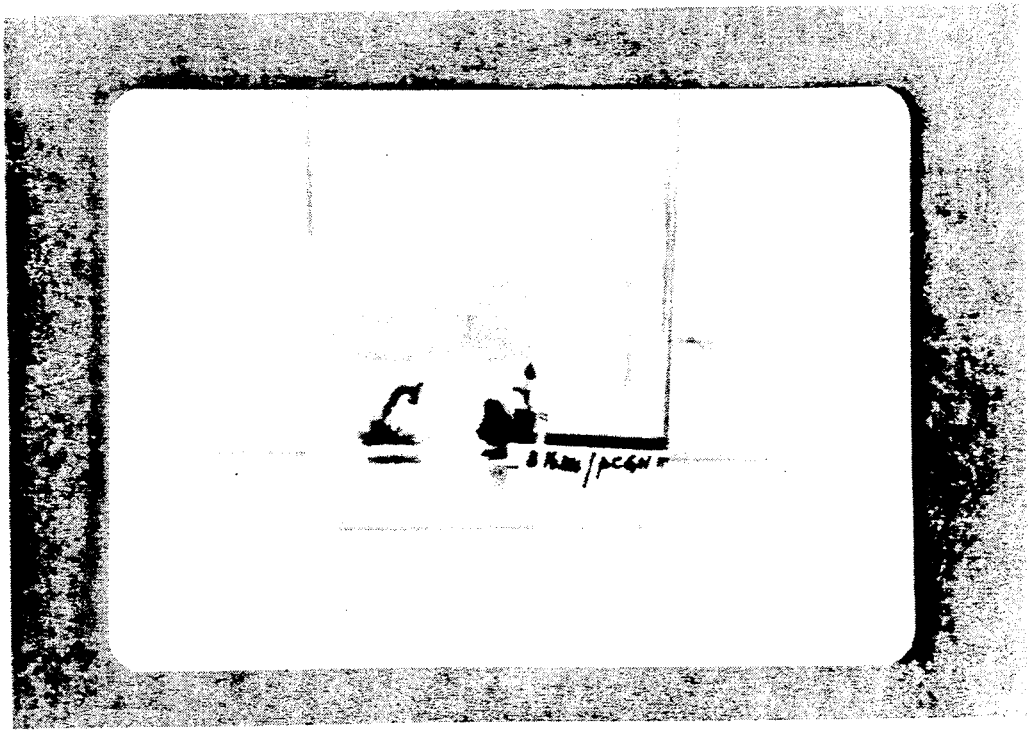
Figure 13:
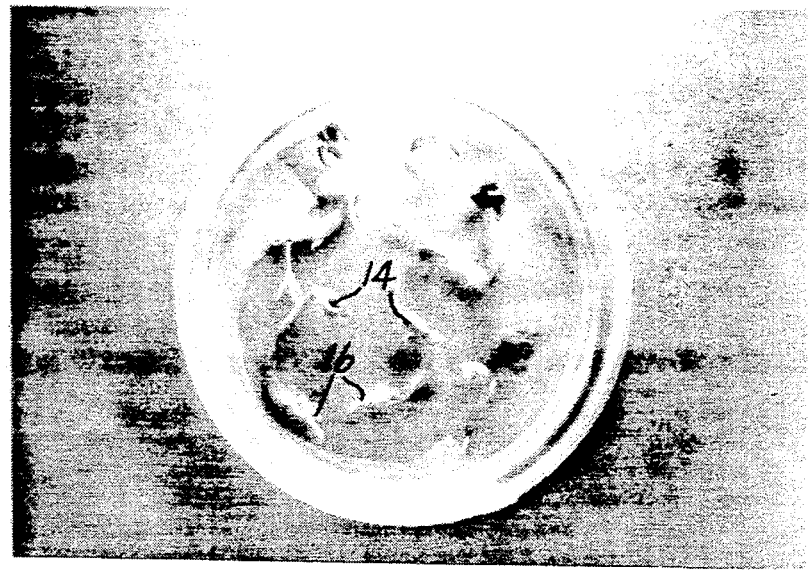
Figure 14:
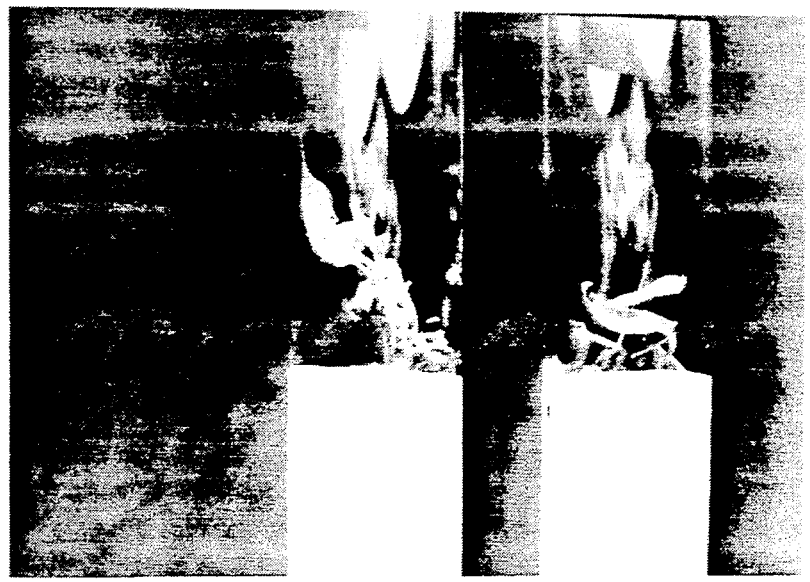
Figure 15:

Using the above procedure and with reference to FIG. 9, there are shown various cell colonies which are a consequence of transformation. There exist cotton cells 20 exhibiting resistance to the antibiotic kanamycin. FIG. 10, shows transformed callus with developing into somatic embryos on an antibiotic MS medium. FIG. 11 shows transformed somatic embryos established to have kanamycin resistance and transformed to have resistance to the herbicide glyphosate. FIG. 12 shows plants from the embryos of FIG. 11 FIG. 13 shows cells transformed to have resistance to lepidopterous insects growing on an MS medium and in FIG. 14 transferred to a Beasley and Ting's medium whereas FIG. 15 shows further development of the plantlets of FIG. 14 to more mature plantlets.

COTTON REGENERATION

Example 1

Regeneration of plants starting from cotyledon explants

Seeds of Acala cotton variety SJ2 of *Gossypium hirsutum* were sterilized by contact with 95% alcohol for three minutes, then twice rinsed with sterile water and immersed with a 15% solution of sodium hypochlorite for 15 minutes, then rinsed in sterile water. Sterilized seeds were germinated on a basal agar medium in the dark for approximately 14 days to produce a seedling. The cotyledons of the seedlings were cut into segments of 2–4mm$^2$, which were transferred aseptically to a callus inducing medium consisting of Murashige and Skoog (MS) major and minor salts supplemented with 0.4 mg/l thiamine-HCl, 30 g/l glucose, 2.0 mg/l naphtaleneacetic acid (NAA), 1 mg/l kinetin, 100 mg/l of m-inositol, and agar (0.8%). The cultures were incubated at about 30° C. under conditions of 16 hours light and 8 hours darkness in a Percival incubator with fluorescent lights (cool daylight) providing a light intensity of about 2000–4000 lux.

Callus formed on the cultured tissue segments within 3 to 4 weeks and were white to gray-greenish in color. The callus formed were subcultured every three to four weeks onto a callus growth medium comprising MS medium containing 100 mg/l m-inositol, 20 g/l sucrose, 2 mg/l naphthaleneacetic acid (NAA) and agar. Somatic embryos formed four to six months after first placing tissue explants on a callus inducing medium. The callus and embryos were maintained on a callus growth medium by subculturing onto fresh callus growth medium every three to four weeks.

Somatic embryos which formed on tissue pieces were explanted either to fresh callus growth medium, or to Beasley & Ting's medium (embryo germination medium).

The somatic plantlets which were formed from somatic embryos were transferred onto Beasley and Ting's medium which contained 1200 mg/l ammonium nitrate and 500 mg/l casein hydrolysate as an organic nitrogen source. The medium was solidified by a solidifying agent (Gelrite) and plantlets were placed in Magenta boxes.

The somatic embryos developed into plantlets within about three months. The plantlets were rooted with six to eight leaves and about three to four inches tall and were transferred to soil and maintained in an incubator under high humidity for three to four weeks and then transferred to a greenhouse. After hardening, plants were also transferred to open tilled soil.

Example 2

The procedure of Example 1 was repeated using instead half-strength MS medium in which all medium components have been reduced to one-half the specified concentration. Essentially the same results were obtained.

Example 3

The procedures of Examples 1 and 2 were repeated except that the explant was the hypocotyl segments. The same results were obtained.

Example 4

The procedure of Examples 1 and 2 were repeated except that the explant was the immature zygotic embryo. Essentially the same results were obtained.

Example 5

The procedure of Examples 1 and 2 was repeated with Acala cotton varieties SJ4, SJ5, SJ2C-1, GC510, B1644, B 2724, B1810, the picker variety Siokra and the stripper variety FC2017. All were successfully regenerated.

Example 6

The procedure of Example 1 was repeated to the extent of obtaining callus capable of forming somatic embryos. Pieces of about 750–1000 mg or actively growing embryogenic callus was suspended in 8 ml units of liquid suspension culture medium comprised of MS major and minor salts, supplemented with 0.4 mg/l thiamine HCl, 20 g/l sucrose, 100 mg/l of inositol and naphthaleneacetic acid (2 mg/l) in T-tubes and placed on a roller drum rotating at 1.5 rpm under 16:8 light::dark regime. Light intensity of about 2000–4500 lux was again provided by fluorescent lights (cool daylight).

After four weeks, the suspension was filtered through an 840 micron size nylon mesh to remove larger cell clumps. The fraction smaller than 840 microns was allowed to settle and washed once with about 20–25 ml of fresh suspension culture medium. This suspension was transferred to T-tubes (2 ml per tube) and each tube diluted with 6 ml of fresh suspension culture medium. The cultures were maintained by repeating the above procedure at 10–12 day intervals. Namely, the suspension was filtered and only the fraction containing cell aggregates smaller than 840 microns was transferred to fresh suspension culture medium. In all instances, the fraction containing cell clumps larger than 840 microns was placed onto the callus growth medium to obtain mature somatic embryos.

The somatic embryos that were formed on callus growth medium were removed and transferred to embryo germination medium and using the protocol of Example 1 were germinated, developed into plantlets and then field grown plants.

Example 7

The procedure of Example 6 was repeated except that suspension cultures were formed by transferring 750–1000 mg of embryogenic calli to a DeLong flask containing 15–20 ml of the MS liquid medium containing 2 mg/l NAA. The culture containing flask was placed on a gyrotory shaker and shaken at 100–110 stroked/minute. After three weeks, the suspension was filtered through an 840 micron nylon mesh to remove the large cell clumps for plant growth, as in Example 4. The less than 840 micron suspension was allowed to settle, washed once in the MS liquid medium and resuspended in 2 to 5 ml of the MS liquid medium. The suspension was subcultured by transfer to fresh medium in a DeLong flask containing 1–2 ml of suspension and 15 ml of fresh MS liquid medium. The cultures were maintained by repeating this procedure at seven to ten day intervals. At each subculture only the less than 840 micron suspension was subcultured and the large clumps (840 microns or greater) were used for plant growth.

Example 8

After three or four subcultures using the suspension growth procedure of Examples 6 and 7, 1.5 to 2.0 ml of cell suspension from the T-tube and DeLong flask were in each instance plated onto agar-solidified MS medium containing 2 mg/l NAA and Beasley & Ting medium containing 500 mg/l casein hydrolysate. Within three to four weeks embryogenic callus with developing embryos became visible. Again, the 840 micron or greater cell clumps were plated on the callus growth medium giving rise to embryogenic clumps with developing embryos which ultimately grew into plants.

COTTON TRANSFORMATION

Example 9

Transformation To Form Tumorous-Phenotype With Agrobacteria LBA 4434

An Acala cotton suspension culture was subcultured for three to four months in T-tubes with the medium (MS medium containing 2 mg/l NAA) being changed every seven to ten days. After any medium change thereafter the cells can be allowed to settle and harvested for transformation. The supernatant was removed by pipeting and cells transformed with the Agrobacterium strain LBA 4434. The Agrobacterium strain LBA 4434 is described in (Hoekema, A. et al. *Nature* 303: 179–180, 1983, incorporated herein by reference) contains a Ti plasmid-derived binary plant transformation system. In such binary systems, one plasmid contains the T-DNA of a Ti-plasmid, the second plasmid contains the vir-region of a Ti-plasmid. The two plasmids cooperate to effect plant transformation. In the strain LBA 4434, the T-DNA plasmid, pAL 1050, contains $T_L$ of pTiAch5, an octopine Ti-plasmid and the vir-plasmid in strain LBA 4404. The strain, pAL44u4, contains the intact virulence regions of pTiAch 5 (Ooms, G. et al. *Plasmid* 7:15–29, 1982, incorporated herein by reference). Strain LBA 4434 is available from Dr. Robert Schilperoort of the Department of Biochemistry, University of Leiden, The Netherlands.

The transforming Agrobacterium strain was taken from a glycerol stock, inoculated in a small overnight culture, from which a 50-ml culture was inoculated the following day. Agrobacteria was grown on YEB medium containing per liter in water adjusted to pH 7.2 with NaOH, 5 g beef extract, 1 g yeast extract, 5 g peptone, 5 g sucrose. After autoclaving, 1 ml of 2 M $MgCl_2$ is added after which antibiotics, as required to kill other strains. The absorbance at 600 nm of the 50 ml overnight culture is read, the culture centrifuged and the formed pellet resuspended in the plant cell growth medium (MS medium plus NAA at 2 mg/l) to a final absorbance at 600 nm of 0.5.

Eight ml of this bacterial suspension of Agrobacterium LBA 4434 was added to each T-tube containing the suspension plant cells after removal of the supernatant liquid. The T-tube containing the plant and bacteria cells was agitated to resuspend the cells and returned to a roller drum for three hours to allow the Agrobacteria to attach to the plant cells. The cells were then allowed to settle and the residual supernatant removed. A fresh aliquot of growth medium was added to the T-tube and the suspension allowed to incubate on a roller drum for a period of 18 to 20 hours in the presence of any residual Agrobacteria which remained. After this time, the cells were again allowed to settle, the supernatant removed and the cells washed twice with a solution of growth medium containing cefotaxime (200 ug/ml). After washing, the cells from each T-tube were resuspended in 10 ml growth medium containing cefotaxime (200 ug/ml in all cases) and 1 ml aliquots of the suspension plated on petri dishes.

Infected cells grew on the growth medium to which no phytohormones were added establishing the tissue had received the wild-type phytohormone genes in T-DNA. The cells developed tumors, further indicating transformation of the cultures.

Example 10

Transformation of Cotton To Form a Kanamycin-Resistant Non-Tumorous Phenotype The suspension culture as obtained in Example 9 was transformed using an Agrobacterium which contained the T-DNA containing binary vector pCIB 10. (Rothstein, S.J. et al. Gene 53: 153–161, 1987, incorporated herein by reference) as well as the pAL 4404 vir-plasmid. The T-DNA of pCIB 10 contains a chimeric gene composed of the promoter from nopaline synthase, the coding region from Tn5 encoding the enzyme neomycin phosphotransferase, and the terminator from nopaline synthase. The Agrobacterium containing pCIB 10 was grown on YEB medium containing kanamycin (50 ug/ml). Transformation was accomplished in the same manner as in Example 10 except that the 1 ml aliquots resulting in cells and Agrobacteria were immediately plated on selective media containing either kanamycin (50 ug/ml) or G418 (25 ug/ml). Expression of the nos-/neo/nos chimeric gene in transformed plant tissue allows the selection of this tissue in the presence of both antibiotics. The existence in two to four weeks of transformed tissue became apparent in the selection plates. Uninfected tissue as well is added control tissue showed no signs of growth, turned brown and died. Transformed tissue grew very well in the presence of both kanamycin and G418.

At this time, tissue pieces which were growing well were subcultured to fresh selection medium. Somatic embryos formed on these tissue pieces and were explanted to fresh non-selective growth media. When the embryos began to differentiate and germinate, i.e., at the point where they were beginning to form roots and had two or three leaves, they were transferred to Magenta boxes containing growth medium described in example 1. Growth was allowed to proceed until a plantlet had six to eight leaves, at which time it was removed from the agar medium.

The plantlets were now placed in potting soil, covered with a beaker to maintain humidity and placed in a Percival incubator for four to eight weeks. At this time, the plant was removed from the beaker and transferred to a greenhouse. The plants grew in the greenhouse, flowered and set seed.

Example 11

The procedure of Example 10 was followed, except that the transforming Agrobacterium used contained the T-DNA vector DEI PEP10 as well as the pAL4404 vir plasmid. DEI PEP10, shown in FIG. 33, utilizes two T-DNA PstI cleaved right border sequences from *A. Tumefaciens* (strain C-58) which had been further subdivided with BamHI for integration in the plant genome, a passenger maize phosphoenolpyruvate carboxylase gene (Pepcase gene), and a chimeric gene (NOS/NPT/TK) capable of expression in plants and conferring resistance to the antibiotics kanamycin and G418. This chimeric gene utilizes a nopaline synthetase promoter, the neomycin phosphotransferase II coding region from Tn5, and the terminator from the herpes simplex virus thimidine kinase gene. Following transformation, embryogenic callus and embryos were obtained by selection on kanamycin (50 mg/l). No resistant callus was obtained from the control (non-transformed callus) plated on kanamycin at this level (50 mg/l).

Example 12

Transformation of Cotton Suspension Culture Cells To A Glyphosate-Tolerant Phenotype The procedure of Example 10 was followed, except that the transforming Agrobacterium used contained the T-DNA vector pPMG85/587 (Fillatti, J. et al., Mol Gen. Genet. 206: 192–199, 1987, incorporated herein by reference) as well as the pAL4404 vir plasmid. The plasmid pPMG85/587 carries three chimeric genes capable of expression in plants. Two genes code for neomycin phosphotransferase (NPT) which confers resistance to the antibiotics kanamycin and G418. The third chimeric gene, containing the coding sequence from a mutant aroA gene of *S. typhimurium*, confers tolerance to the herbicide glyphosate (Comai, et al., Science 221: 370–371, 1983, incorporated herein by reference). The Agrobacterium containing pPMG85/587 was grown on medium containing kanamycin (100 ug/ml). Transformation was accomplished as detailed in Example 10 except that the suspension was allowed to grow for 28 days at which time 1 ml aliquots were plated on medium containing selective antibiotics. Expression of the NPT chimeric gene in transformed plant tissue allowed selection of this tissue on both antibiotics. In this instance the selective antibiotic was kanamycin (50 ug/ml).

In two to four weeks, transformed tissue became apparent on the selection plates. Plant tissue, individual embryos and callus were then placed on growth medium containing the herbicide glyphosate 1mM and transformed tissue continued to grow well. Extraction and analysis of the proteins of both callus and embryos confirmed the presence of the product of the glyphosate tolerance gene.

Example 13

Transformation of Cotton Suspension Culture Cells To a Hygromycin-Resistant Non-Tumorous Phenotype The transformation procedure of Example 10 was followed except there was used as the transforming Agrobacterium one containing the T-DNA binary vector pCIB 715 (Rothstein, S. J. et al. *Gene* 53: 153–161, 1987) as well as the vir plasmid. The T-DNA of pCIB 715 contains a chimeric gene composed of the promoter and terminator from the cauliflower mosaic virus (CaMV) 35S transcript (Odell et al, Nature 313: 810–812, 1985, incorporated herein by reference) and the coding sequence for hygromycin B phosphotransferase (Gritz, L. and J. Davies, Gene 25: 179–188, incorporated herein by reference). The Agrobacterium containing pCIB 715 was grown on YEB containing kanamycin (50 ug/ml).

Transformation was accomplished as detailed in Example 10 again with the change that the 1 ml aliquots were plated immediately on medium containing as the selective antibiotic 50 ug/ml hygromycin. Expression of the chimeric hygromycin gene in transformed plant tissue allowed the selection of this tissue on the medium containing hygromycin. Transformed tissue was grown in the manner described in Example 8 on the selection growth medium establishing transformation had occurred.

Example 14

Transformation of Cotton Suspension Culture Cells To Confer Resistance To Lepidopteran Insects The procedure of Example 10 was followed except where changes are noted below. Different transforming Agrobacterium was used. Also, after plant tissue was selected on an antibiotic for the selection of transformed material, it was further selected for expression of the BT gene as defined herein.

Figure 16:
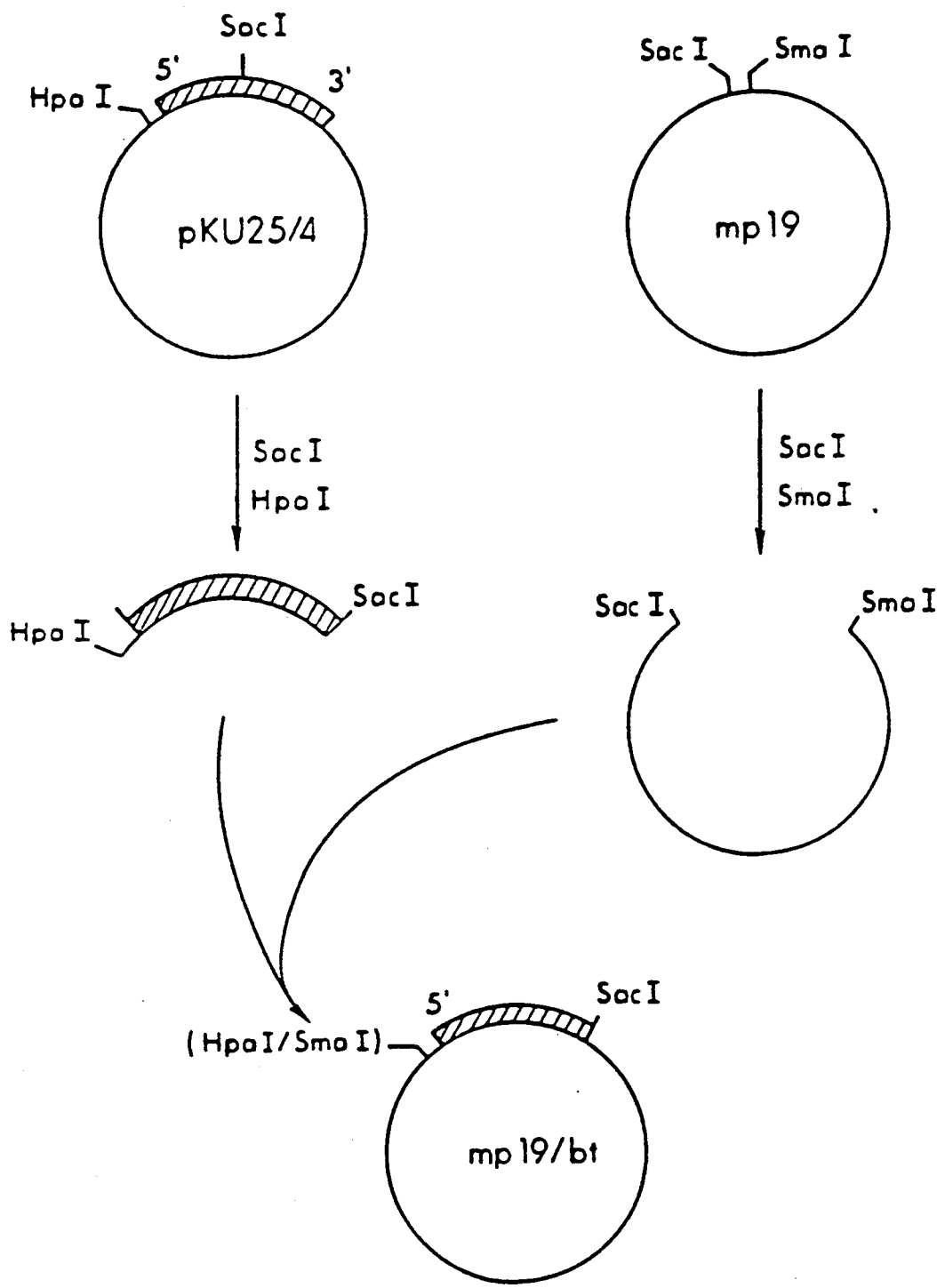
FIG. 16 shows the construction of mp 19/bt, a plasmid containing the 5' end of the Bt protoxin gene.
Figure 17:
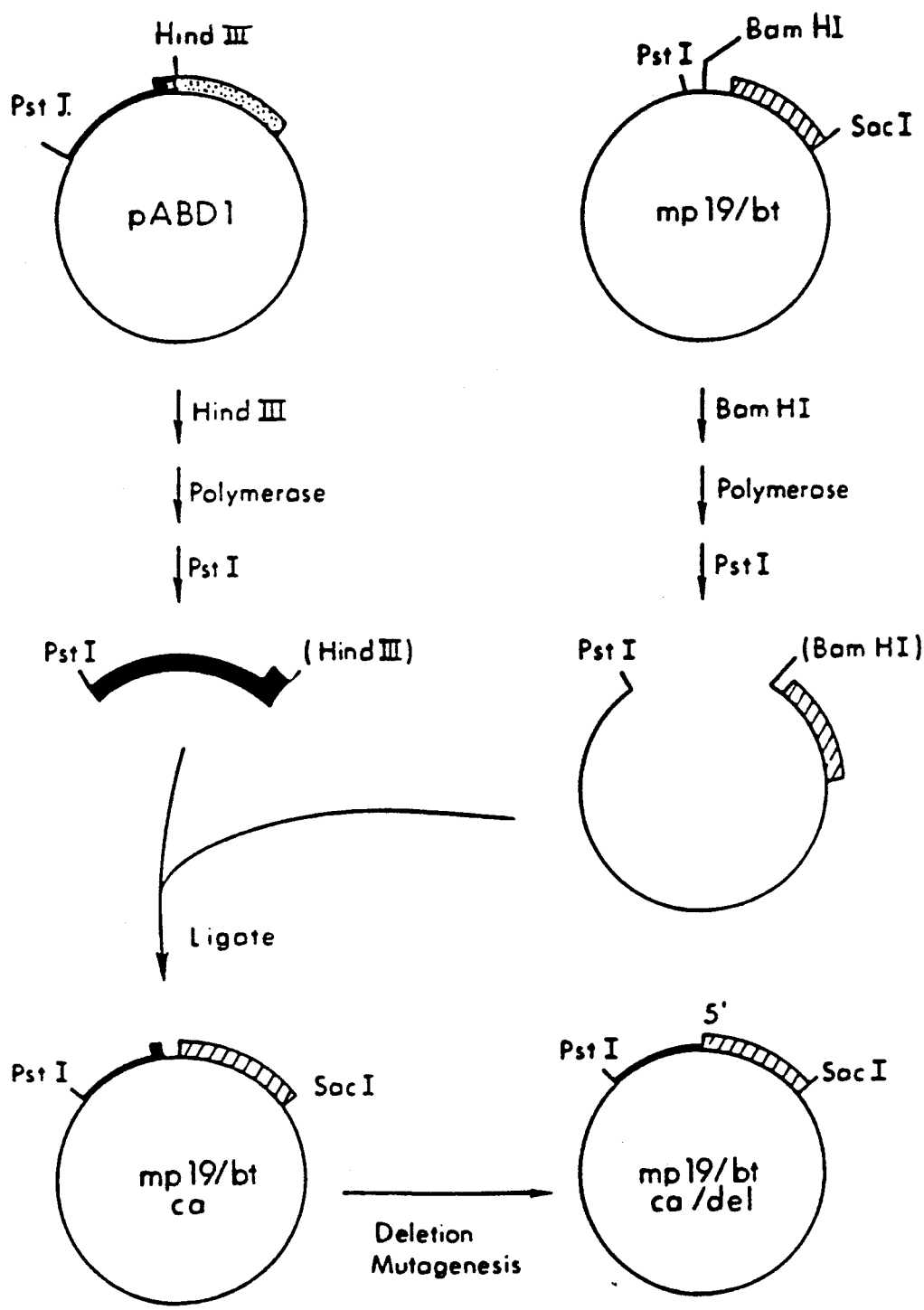
FIG. 17 shows the construction of mp 19/bt ca/del, a plasmid containing the CaMV gene VI promotor fused to the 5' end of Bt protoxin coding sequence.
Figure 18:
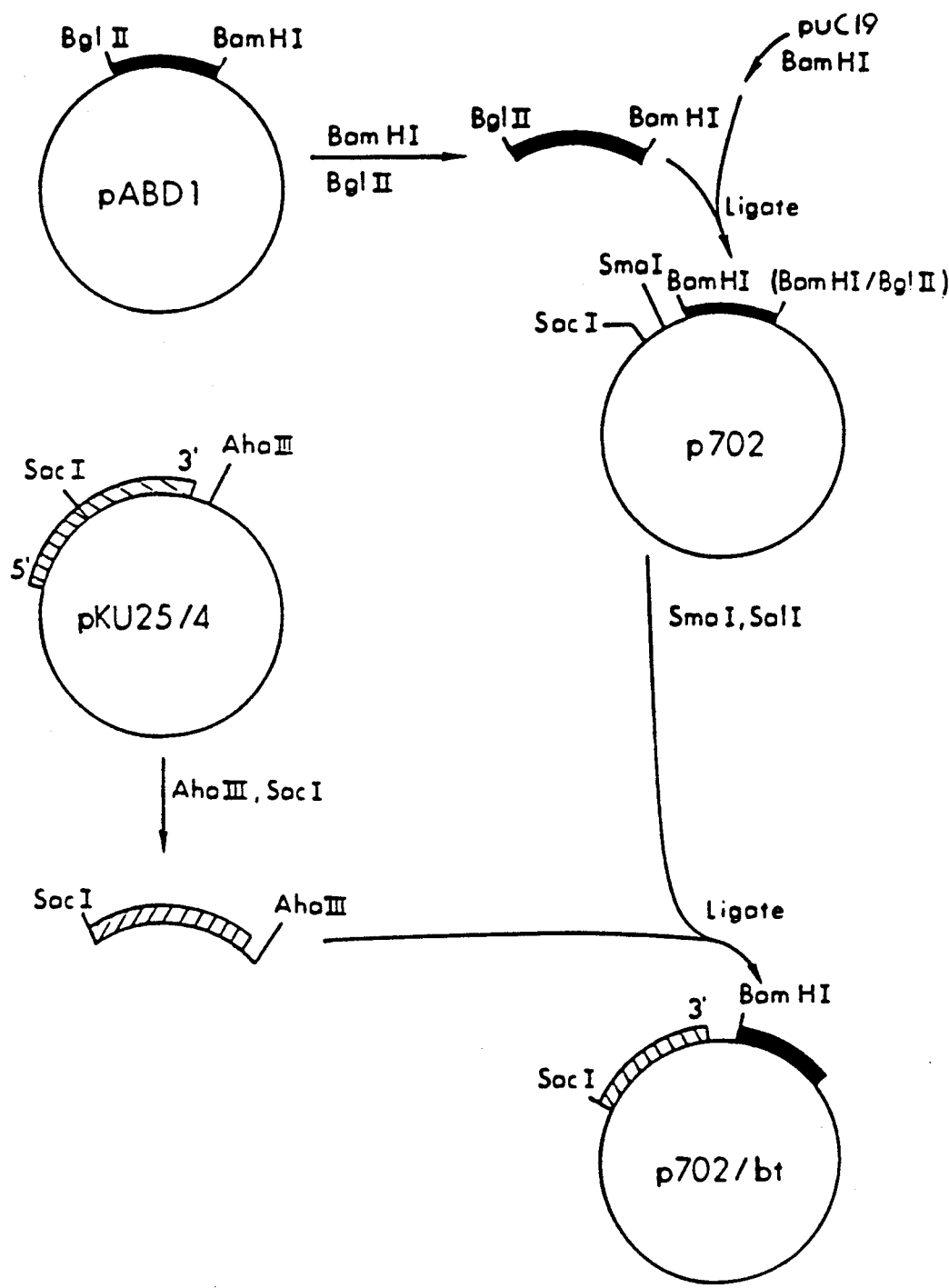
FIG. 18 shows the construction of p702/bt, a plasmid having the 3' coding region of the protoxin fused to the CaMV transcription termination signals.

The Agrobacterium used contained the T-DNA vector pCIB10 (Rothstein et al, Gene 53:153-161 (198)) incorporated herein by reference into which had been inserted the following chimeric *Bacillus thuringiensis* endotoxin genes ("BT Genes"):

To prepare the Agrobacterium vector there was fused the CaMV gene VI promotor and protoxin coding sequences. A derivative of phage vector mp19 (Yanish-Perron et al., 1985) was first constructed. The steps are shown in FIGS. 16 and 17. First, a DNA fragment containing approximately 155 nucelotides 5' to the protoxin coding region and the adjacent approximately 1346 nucleotides of coding sequence was inserted into mp19. Phage mp19 ds rf (double-stranded replicative form) DNA was digested with restriction endonucleases SacI and SmaI and the approximately 7.2-kbp vector fragment was purified after electrophoresis through low-gelling temperature agarose by standard procedures. Plasmid pKU25/4, containing approximately 10 kbP (kilobase pairs) of *Bacillus thuringiensis* DNA, including the protoxin gene, was obtained from Dr. J. Nueesch, CIBA-Geigy Ltd., Basle, Switzerland. The nucleotide sequence of the protoxin gene present in plasmid pkU25/4 is shown in Formula 1 below. Plasmid pKU25/4 DNA was digested with endonucleases HpaI and SacI, and a 1503 bp fragment containing nucleotides 2 to 1505 of Formula 1 and purified. This fragment contains approximately 155 bp of bacteria promotor sequences and approximately 1346 bp of the start of the protoxin coding sequence. Approximately 100 ng of each fragment was then mixed, T4 DNA ligase added, and incubated at 15° C. overnight. The resulting mixture was transformed into *E. coli* strain HB 101, mixed with indicator bacteria *E. coli* JM 101 and plated. One phage (mp19/bt) was used for further construction below.

Figure 19:
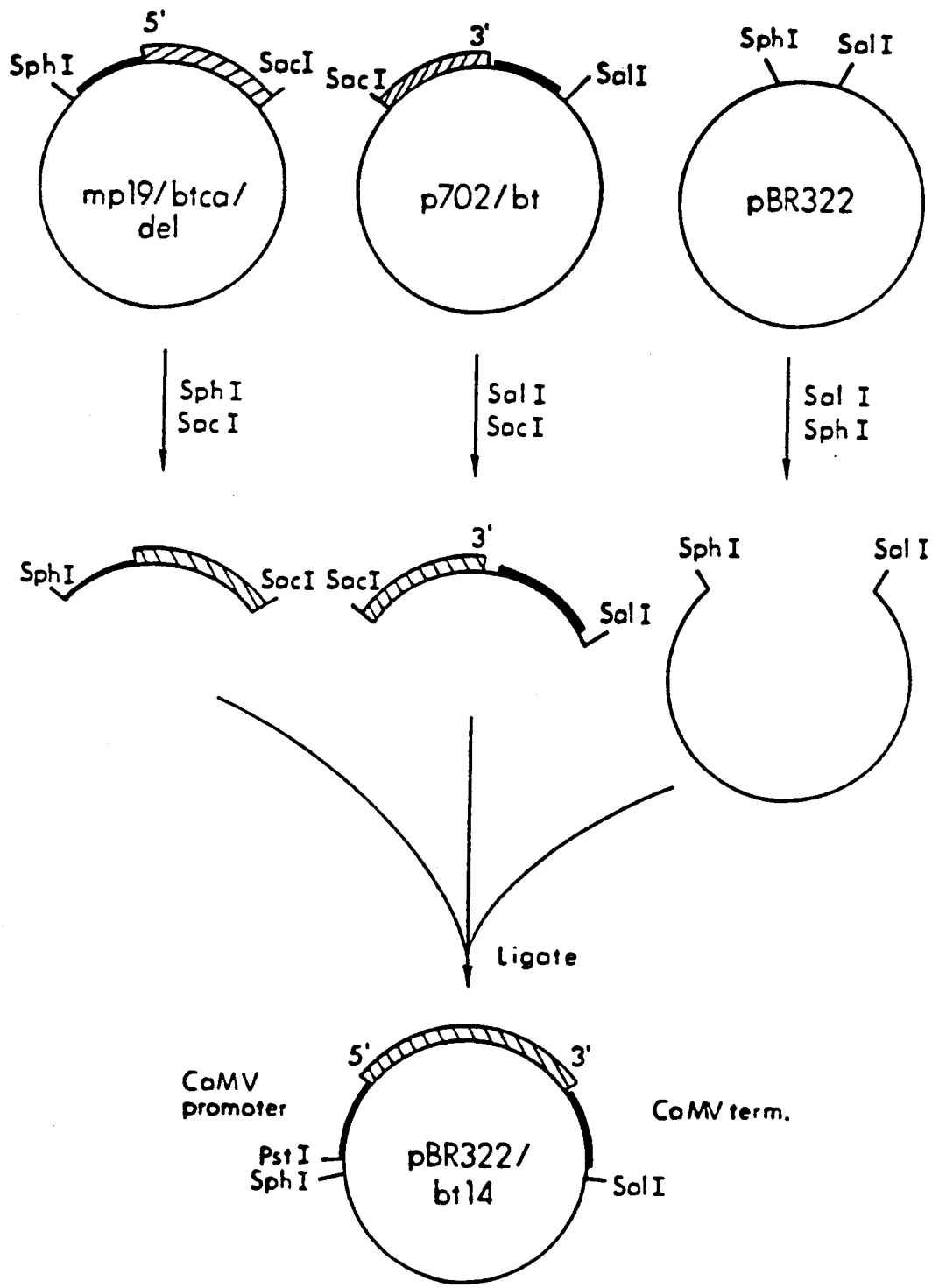
FIG. 19 shows the construction of pBR322/bt 14, containing the complete protoxin coding sequence flanked by CaMV promotor and terminator sequences.

Next, a fragment of DNA containing the CaMV gene VI promotor, and some of the coding sequences for gene VI, was inserted into mp19/bt. Phage mp19/bt ds rf DNA was digested with BamHI, treated with the large fragment of DNA polymerase to create flush ends and recleaved with endonuclease PstI. The larger vector fragment was purified by electrophoresis as described above. Plasmid pABDI is described in Paszkowski et al., EMBO J. 3, 2717-2722, (1984) incorporated herein by reference. Plasmid pABD1 DNA was digested with PstI and HindIII. The fragment approximately 465 bp long containing the CaMV gene VI promotor and approximately 75 bp of gene VI coding sequence was purified. The two fragments were ligated and plated as described above. One of the resulting recombinant phages, mp19/btca contained the CaMV gene VI promotor sequences, a portion of the gene VI coding sequence, approximately 155 bp of Bacillus thuringiensis DNA upstream of the protoxin coding sequence, and approximately 1346 bp of the protoxin coding sequence. To fuse the CaMV promotor sequences precisely to the protoxin coding sequences, the intervening DNA was deleted using oligionicleotide-directed mutagensis of mp19/btca DNA. A DNA oligonucleotide with the sequence (5') TTCGGATTGT-TATCCATGGTTGGAGGTCTGA (3) was synthesized by routine procedures using an Applied Biosystems DNA Synthesizer. This oligonucleotide is complimentary to those sequences in phage mp19/btca DNA at the 3' end of the CaMV promotor (nucleotides 5762 to 5778 in Hohn, Current Topics, in Microbiology and Immunology, 96, 193-235 (1982) incorporate herein by reference and the beginning of the protoxin coding sequence (nucleotides 156 to 172 in formula I above). The general procedure for the mutagensis was that described in Zoller and Smith, Meth, Enzym., 100 468–500 (1983) incorporated herein by reference. Approximately five micrograms of single-stranded phage mp19/btca DNA was mixed with 0.3 mg of phosphorylated oligonucleotide in a volume of 40 ul. The mixture was heated to 65° C. for 5 min, cooled to 50° C., and slowly cooled to 4° C. Next, buffer, nucleotide triphosphates, ATP, $T_4$ DNA ligase and large fragment of DNA polymerase were added and incubated overnight at 15° C. as described [Zoller and Smith Meth. Enzym., 100, 468–500 (1983)] incorporated herein by reference. After agarose gel electrophoresis, circular double-stranded DNA was purified and transfected into *E. coli* strain JM101. The resulting plaques were screened for sequences that hybridize with 32P-labeled oligonucleotide, and phage were analyzed by DNA restriction endonuclease analysis. Among the resulting phage clones were ones which has correctly deleted the unwanted sequences between the CaMV gene VI promotor and the protoxin coding sequence. This phage is called mp19/btca/del (see FIG. 17).

Next, a plasmid was constructed in which the 3′ coding region of the protoxin gene was fused to CaMV transcription termination signals. The steps are shown in FIG. 18. First, plasmid pABDI DNA was digested with endonucleases BamHI and BglII and a 0.5 kbp fragment containing the CaMV transcription terminator sequences isolated. Next plasmid pUC19, Yanisch-Perron et al., Gene, 33, 103–119 (1985) incorporated herein by reference was digested with BamHI, mixed with the 0.5 kbp fragment and incubated with $T_4$ DNA ligase. After transformation of the DNA into *E. coli* strain HB1O1, one of the resulting clones, called plasmid p702, was obtained which has the structure shown in FIG. 18. Next, plasmid p702 DNA was cleaved with endonucleases SacI and SmaI, and the larger, approximately 3.2 kbp fragment isolated by gel electrophoresis. Plasmid pKU25/4 DNA was digested with endonucleases AhaIII and SacI, and the 2.3-kbp fragment (nucleotides 1502 to 3773 of Formula 1) containing the 3′ portion of the protoxin coding sequence (nt 1504 to 3773) was isolated after gel electrophoresis. These two DNA fragments were mixed, incubated with $T_4$ DNA ligase and transformed into *E. coli* strain HB101. The resulting plasmid was p702/bt (FIG. 18).

Finally, portions of phage mp19/btca/del ds rf DNA and plasmid p702/bt were joined to create a plasmid containing the complete protoxin coding sequence flanked by CaMV promoter and terminator sequences (see FIG. 18). Phage mp19/btca/del DNA was digested with endonucleases SacI and SphI, and a fragment of approx. 1.75 kbp was purified following agarose gel electrophoresis. Similarly, plasmid p702/bt DNA was digested with endonucleases SacI and SalI and a fragment of approximately 2.5 kbp was isolated. Finally, plasmid pBR 322 DNA (Bolivar et al., Gene, 2, 95–113 (1977) incorporated herein by reference was digested with SalI and SphI and the larger 4.2-kbp fragment isolated. All three DNA fragments were mixed and incubated with T4 DNA ligase and transformed into *E. coli* strain HB101. The resulting plasmid, PBR322/bt14 is a derivative of PBR322 containing the CaMV gene VI promoter and translation start signals fused to the Bacillus thuringiensis crystal protein coding sequence, followed by CaMV transcription termination signals (shown in FIG. 19).

The vector pCIB10 is a Ti-plasmid-derived vector useful for transfer of the chimeric gene to plants via Agrobacterium tumefaciens. The vector is derived from the broad host range plasmid pRK 252, which may be obtained from Dr. W. Barnes, Washington University, St. Louis, Mo. The vector also contains a gene for kanamycin resistance in Agrobacterium, from Tn903, and left and right T-DNA border sequences from the Ti plasmid pTiT37. Between the border sequences are the polylinker region from the plasmid pUC18 and a chimeric gene that confers kanamycin resistance in plants.

Figure 20:
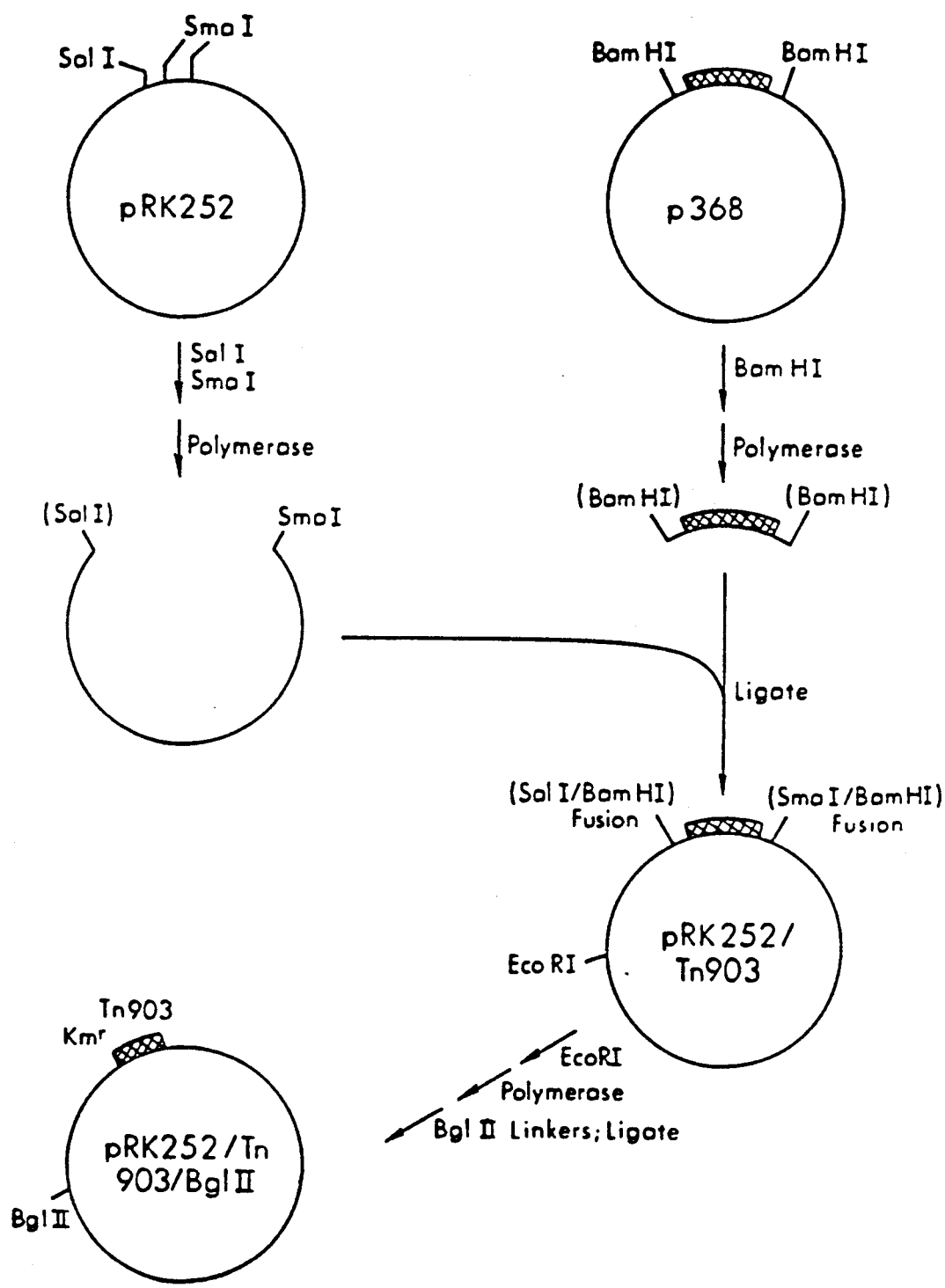
FIG. 20 shows the construction of pRK252/Tn903/BglII.

First, plasmid pRK252 was modified to replace the gene conferring tetracycline-resistance with one conferring resistance to kanamycin from the transposon Tn903 [Oka, et al., J. Mol. Biol., 147, 217–226 (1981) incorporated herein by reference], and was also modified by replacing the unique EcoRI site in pRK252 with a BglII site (see FIG. 20 for a summary of these modifications). Plasmid pRK252 was first digested with endonucleases SalI and SmaI, then treated with the large fragment of DNA polymerase I to create flush ends, and the large vector fragment purified by agarose gel electrophoresis. Next, plasmid p368 was digested with endonuclease BamHI, treated with the large fragment of DNA polymerase, and an approximately 1050-bp fragment isolated after agarose gel electrophoresis; this fragment containing the gene from transposon Tn903 which confers resistance to the antibiotic kanamycin [Oka et al., J. Mol. Biol., 147. 217–226 (1981) incorporated herein by reference]. Both fragments were then treated with the large fragment of DNA polymerase to create flush ends. Both fragments were mixed and incubated with T4 DNA ligase overnight at 15° C. After transformation into *E. coli* strain HB101 and selection for kanamycin resistant colonies, plasmid pRK252/Tn903 was obtained (see FIG. 19).

Plasmid pRK252/Tn903 was digested at its EcoRI site, followed by treatment with the large fragment of *E. coli* DNA polymerase to create flush ends. This fragment was added to synthetic BglII restriction site linkers, and incubated overnight with T4 DNA ligase. The resulting DNA was digested with an excess of BglII restriction endonuclease and the larger vector fragment purified by agarose gel electrophoresis. The resulting fragment was again incubated with T4 DNA ligase to recircularize the fragment via its newly-added BglII cohesive ends. Following transformation into *E. coli* strain HB101, plasmid pRK252/Tn903/BglII was obtained (see FIG. 20).

Figure 21:
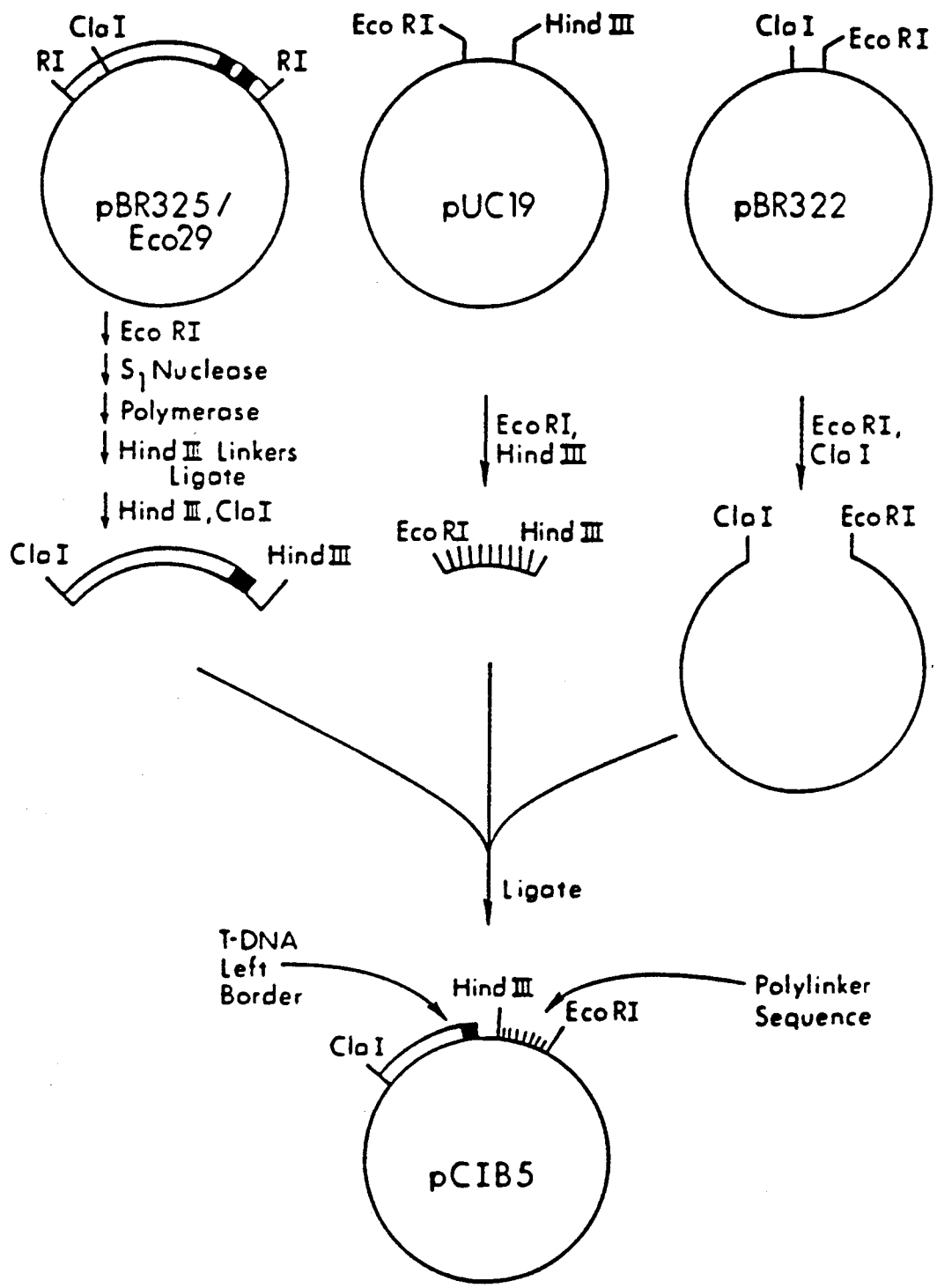
FIG. 21 shows the construction of PCIB 5.

A derivative of plasmid pBR322 was constructed which contains the Ti plasmid T-DNA borders, the polylinker region of plasmid pUC19, and the selectable gene for kanamycin resistance in plants (see FIG. 21). Plasmid pBR325/Eco29 contains the 1.5-kbp EcoRI fragment from the nopaline Ti plasmid pTiT37. This fragment contains the T-DNA left border sequence; Yadav et al., Proc. Natl. Acad. Sci. USA, 79, 6322–6326 (1982) incorporated herein by reference. To replace the EcoRI ends of this fragment with HindIII ends, plasmid pBR325/Eco29 DNA was digested with EcoRI, then incubated with nuclease S1, followed by incubation with the large fragment of DNA polymerase to create flush ends, then mixed with synthetic HindIII linkers and incubated with T4 DNA ligase. The resulting DNA was digested with endonucleases ClaI and an excess of HindIII, and the resulting 1.1-kbp fragment containing the T-DNA left border purified by gel electrophoresis. Next, the polylinker region of plasmid pUC19 was isolated by digestion of the plasmid DNA with endonucleases EcoRI and HindIII and the smaller fragment (approx. 53 bp) isolated by agarose gel electrophoresis. Next, plasmid pBR322 was digested with endonucleases EcoRI and ClaI, mixed with the other two isolated fragments, incubated with T4 DNA ligase and transformed into *E. coli* strain HB101. The resulting plasmid, pCIB5, contains the polylinker and T-DNA left border in a derivative of plasmid pBR322 (see FIG. 21).

Figure 22:
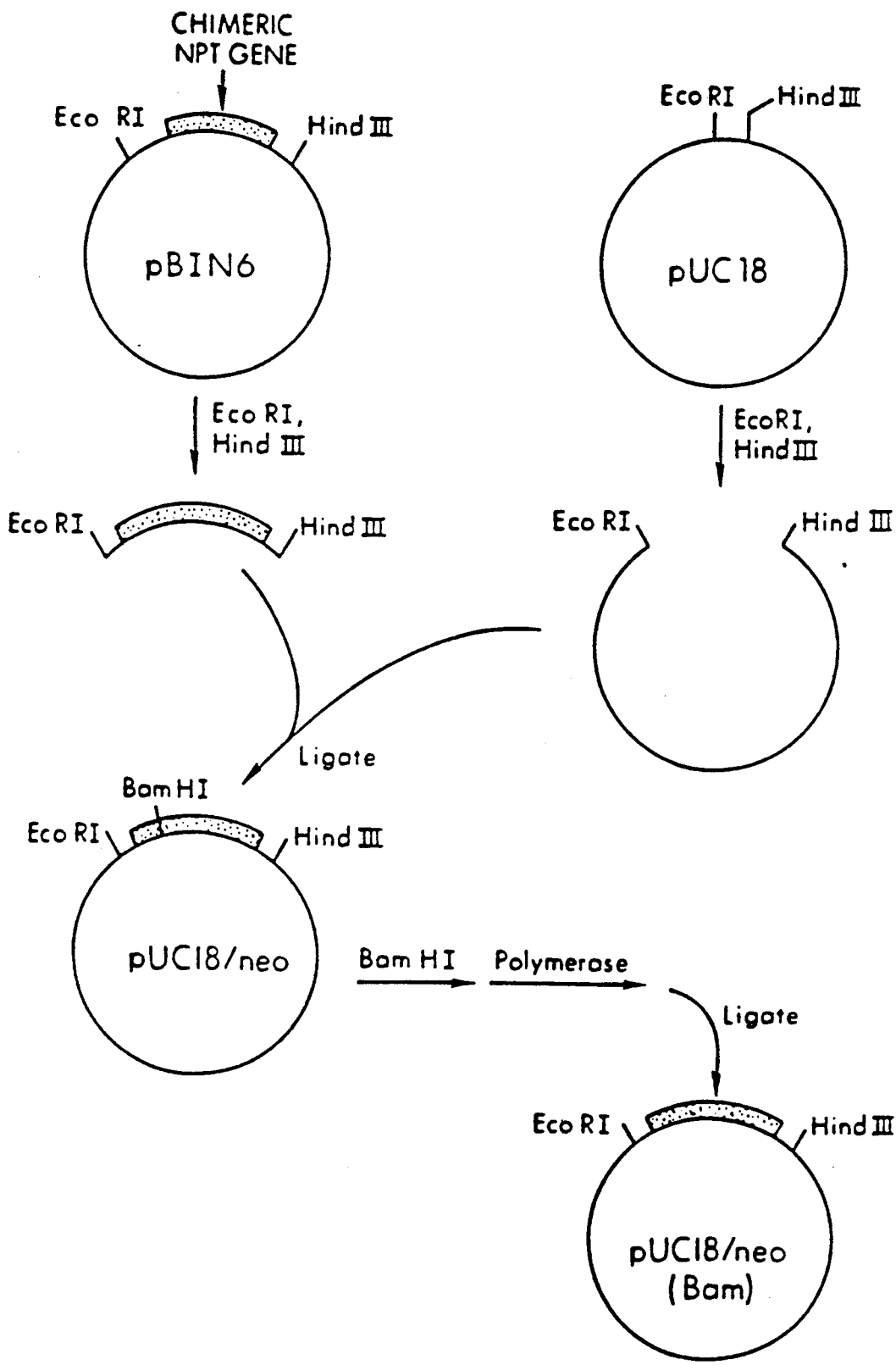
FIGS. 22 & 23 show the construction of pCIB 4.
Figure 23:
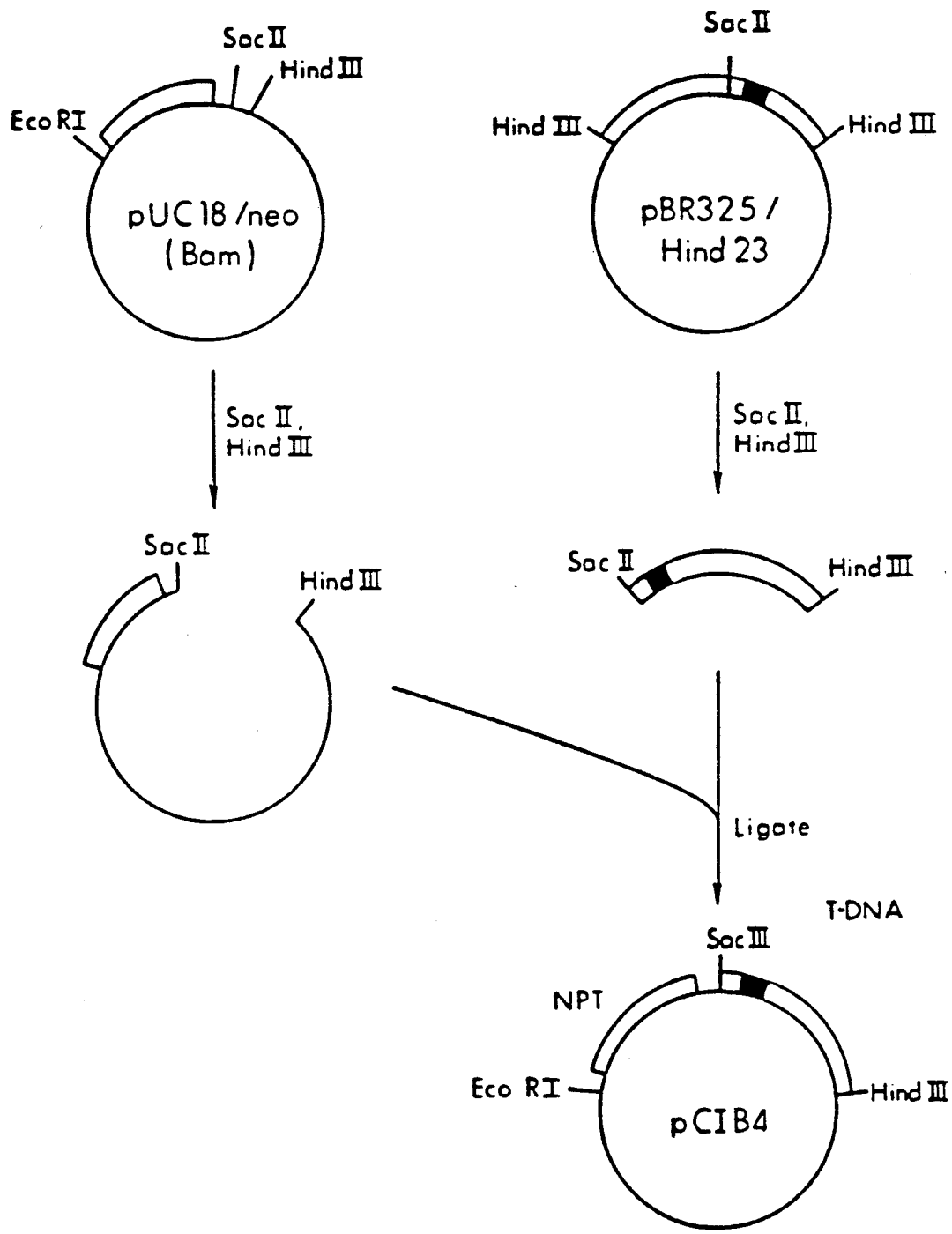

A plasmid containing the gene for expression of kanamycin resistance in plants was constructed (see FIGS. 22 and 23). Plasmid Bin6 obtained from Dr. M. Bevan, Plant Breeding Institute, Cambridge, UK. This plasmid is described in the reference by Bevan, Nucl. Acids Res., 12, 8711–8721 (1984) incorporate herein by reference. Plasmid Bin6 DNA was digested with EcoRI and HindIII and the fragment approximately 1.5 kbp in size containing the chimeric neomycin phosphotransferase (NPT) gene was isolated and purified following agarose gel electrophoresis. This fragment was then mixed with plasmid pUC18 DNA which had been cleaved with endonucleases EcoRI and HindIII. Following incubation with T4 DNA ligase, the resulting DNA was transformed into *E. coli* strain HB101. The resulting plasmid is called pUC18/neo. This plasmid DNA contained an unwanted BamHI recognition sequence between the neomycin phosphotransferase gene and the terminator sequence for nopaline synthase; see Bevan, Nucl. Acids Res., 12, 8711–8721 (1984) incorporated herein by reference. To remove this recognition sequence, plasmid pUC18/neo was digested with endonuclease BamHI, followed by treatment with the large fragment of DNA polymerase to create flush ends. The fragment was then incubated with T4 DNA ligase to recircularize the fragment, and transformed into *E. coli* strain HB101. The resulting plasmid, pUC18/neo(Bam) has lost the BamHI recognition sequence.

Figure 24:
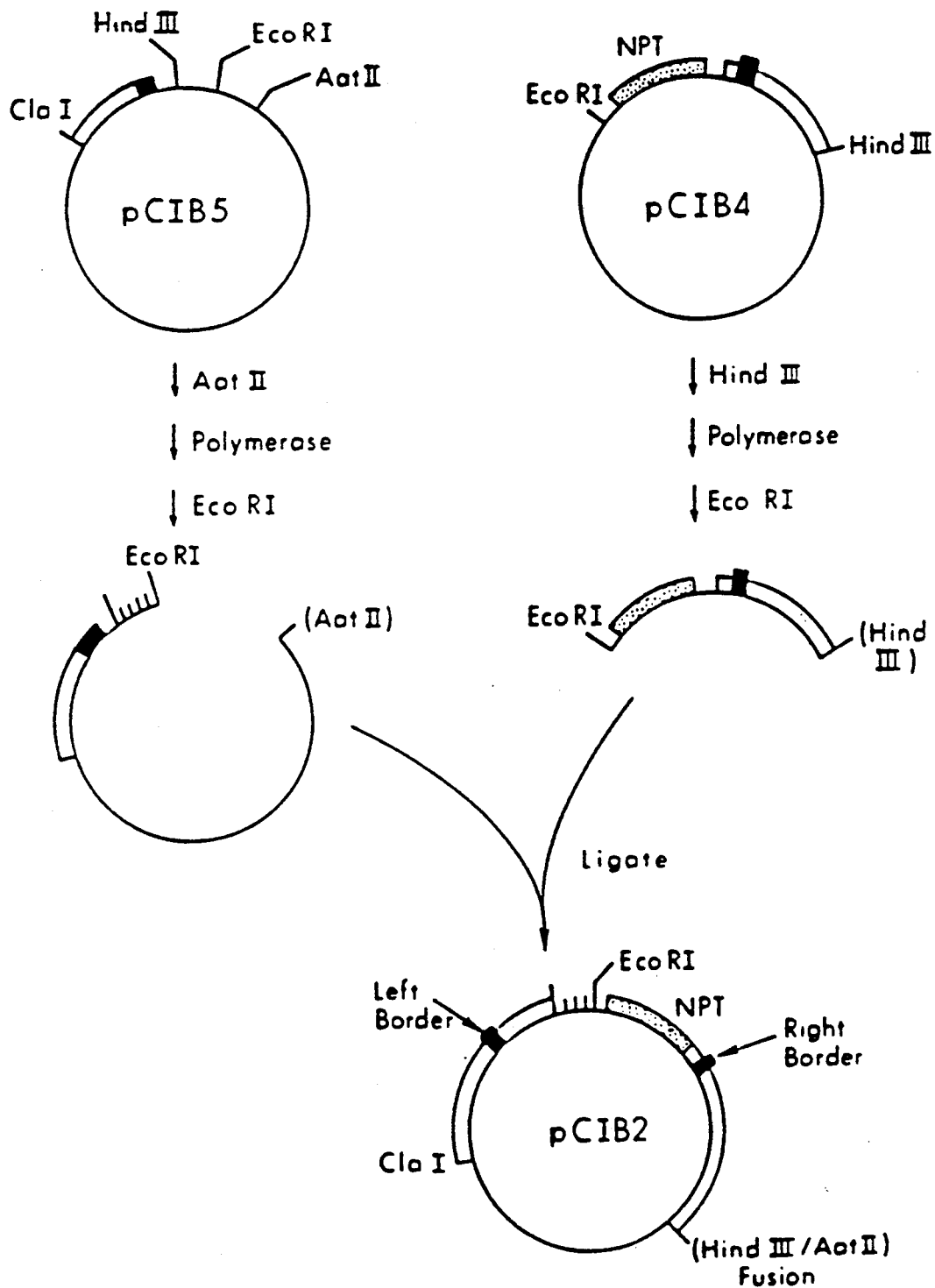
FIG. 24 shows the construction of pCIB 2.

The T-DNA right border sequence was then added next to the chimeric NPT gene (see FIG. 24). Plasmid pBR325/Hind23 contains the 3.4-kbp HindIII fragment of plasmid pTiT37. This fragment contains the right T-DNA border sequence; Bevan et al., Nucl, Acids Res., 11, 369–385 incorporated herein by reference. Plasmid pBR325/Hind23 DNA was cleaved with endonucleases SacII and HindIII, and a 1.0 kbp fragment containing the right border isolated and purified following agarose gel electrophoresis. Plasmid pUC18/neo(-Bam) DNA was digested with endonucleases SacII and HindIII and the 4.0 kbp vector fragment isolated by agarose gel electrophoresis. The two fragments were mixed, incubated with T4 DNA ligase and transformed into *E. coli* strain HB101. The resulting plasmid, pCIB4 (shown in FIG. 23), contains the T-DNA right border and the plant-selectable marker for kanamycin resistance in a derivative of plasmid pUC18.

Figure 28:
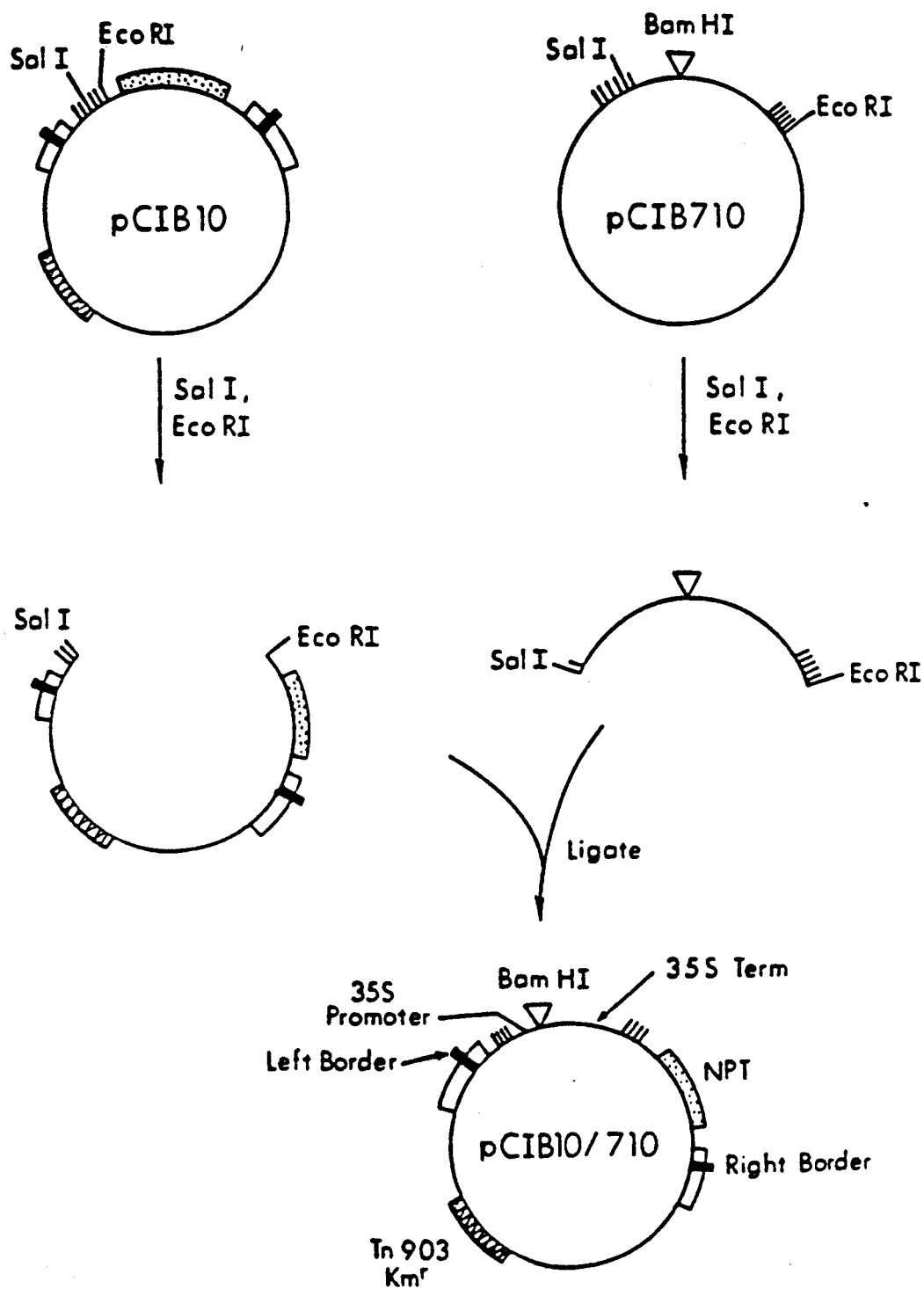
FIG. 28 shows the construction of pCIB10/710.

Next, a plasmid was constructed which contains both the T-DNA left and right borders, with the plant selectable kanamycin-resistance gene and the polylinker of pUC18 between the borders (see FIG. 28). Plasmid pCIB4 DNA was digested with endonuclease HindIII, followed by treatment with the large fragment of DNA polymerase to create flush ends, followed by digestion with endonuclease EcoRI. The 2.6-kbp fragment containing the chimeric kanamycin-resistance gene and the right border to T-DNA was isolated by agarose gel electrophoresis. Plasmid pCIB5 DNA was digested with endonuclease AatII, treated with T4 DNA polymerase to create flush ends, then cleaved with endonuclease EcoRI. The larger vector fragment was purified by agarose gel electrophoresis, mixed with the pCIB4 fragment, incubated with T4 DNA ligase, and transformed into *E. coli* strain HB101. The resulting plasmid, pCIB2 (shown in FIG. 24) is a derivative of plasmic pBR322 containing the desired sequences between the two T-DNA borders.

Figure 25:
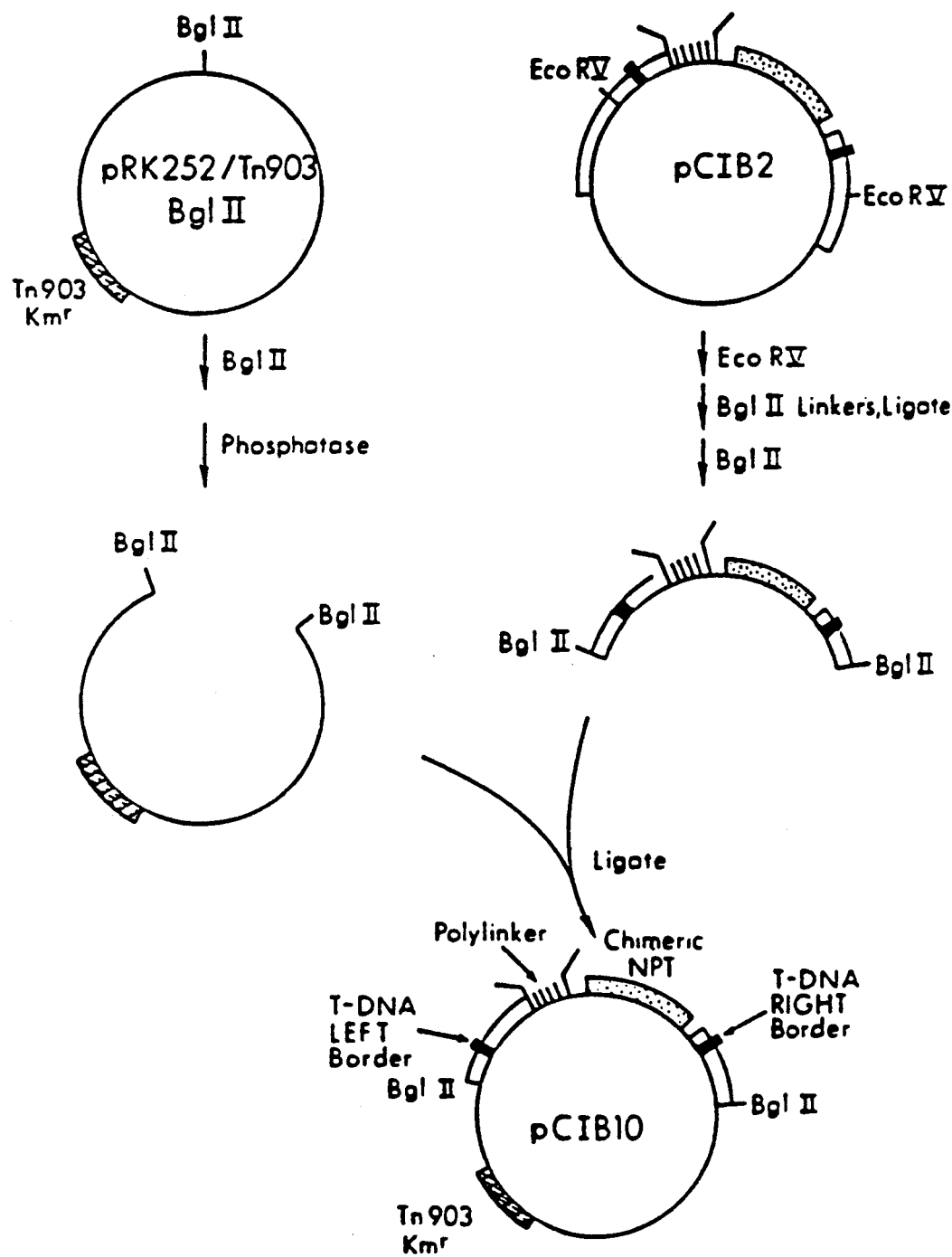
FIG. 25 shows the construction of pCIB 10, a broad host range plasmid containing T-DNA borders and gene for plant selection.

The following steps complete construction of the vector pCIB10, and are shown in FIG. 25. Plasmid pCIB2 DNA was digested with endonuclease EcoRV, and synthetic linkers containing BglII recognition sites are added as described above. After ,digestion with an excess of BglII endonuclease, the approximately 2.6-kbp fragment was isolated after agarose gel electrophoresis. Plasmid pRK252/Tn903/BglII, described above (see FIG. 20) was digested with endonuclease BglII and then treated with phosphatase to prevent recircularization. These two DNA fragments are mixed, incubated with T4 DNA ligase and transformed into *E. coli* strain HB101. The resulting plasmid is the completed vector, pCIB10.

Figure 26:
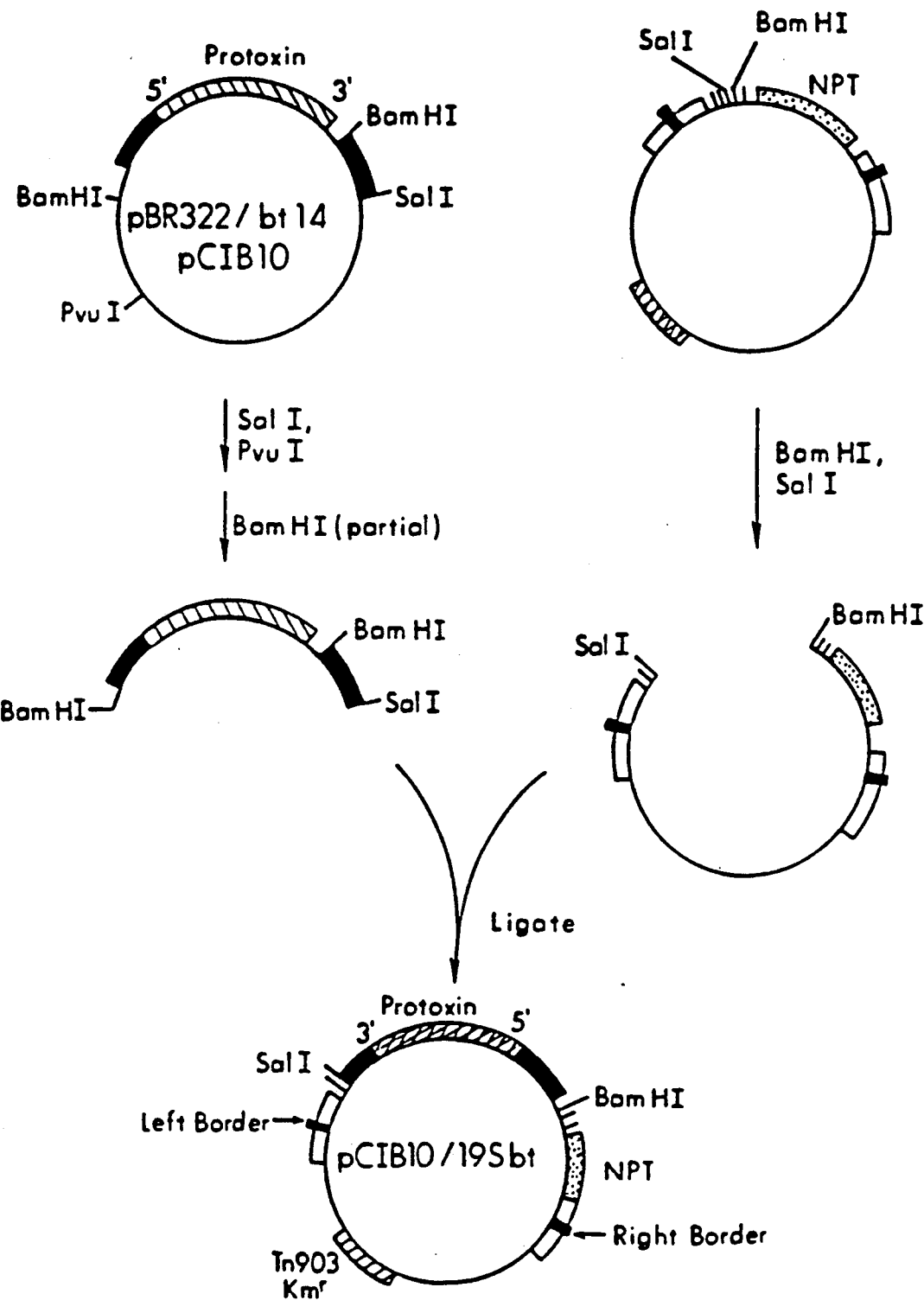
FIG. 26 shows the construction of pCIB10/19Sbt.
Figure 27:
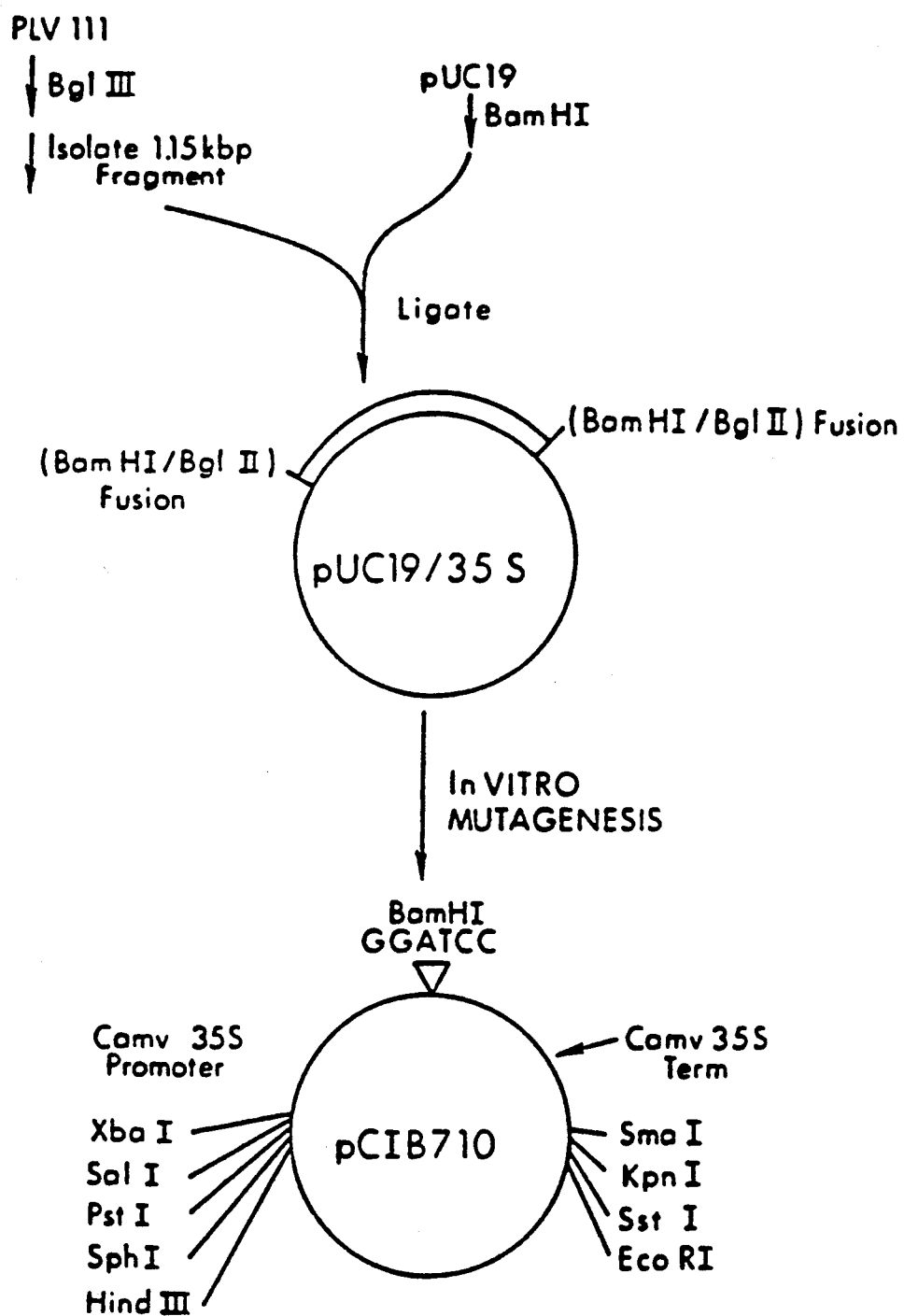
FIG. 27 shows the construction of pCIB 710.

Insertion of the chimeric protoxin gene into vector pCIB10 was by the steps shown in FIG. 26. Plasmid pBR322/bt14 DNA was digested with endonucleases PvuI and SalI, and then partially digested with endonuclease BamHI. A BamHI-SalI fragment approx. 4.2 kbp in size, containing the chimeric gene, was isolated following agarose gel electrophoresis, and mixed with plasmid pCIB10 DNA which had been digested with endonucleases BamHI and SalI. After incubation with T4 DNA ligase and transformation into *E. Coli* strain HB101, plasmid shown in FIG. 26 and contained the chimeric protoxin gene in the plasmid vector pCIB10.

Figure 29:
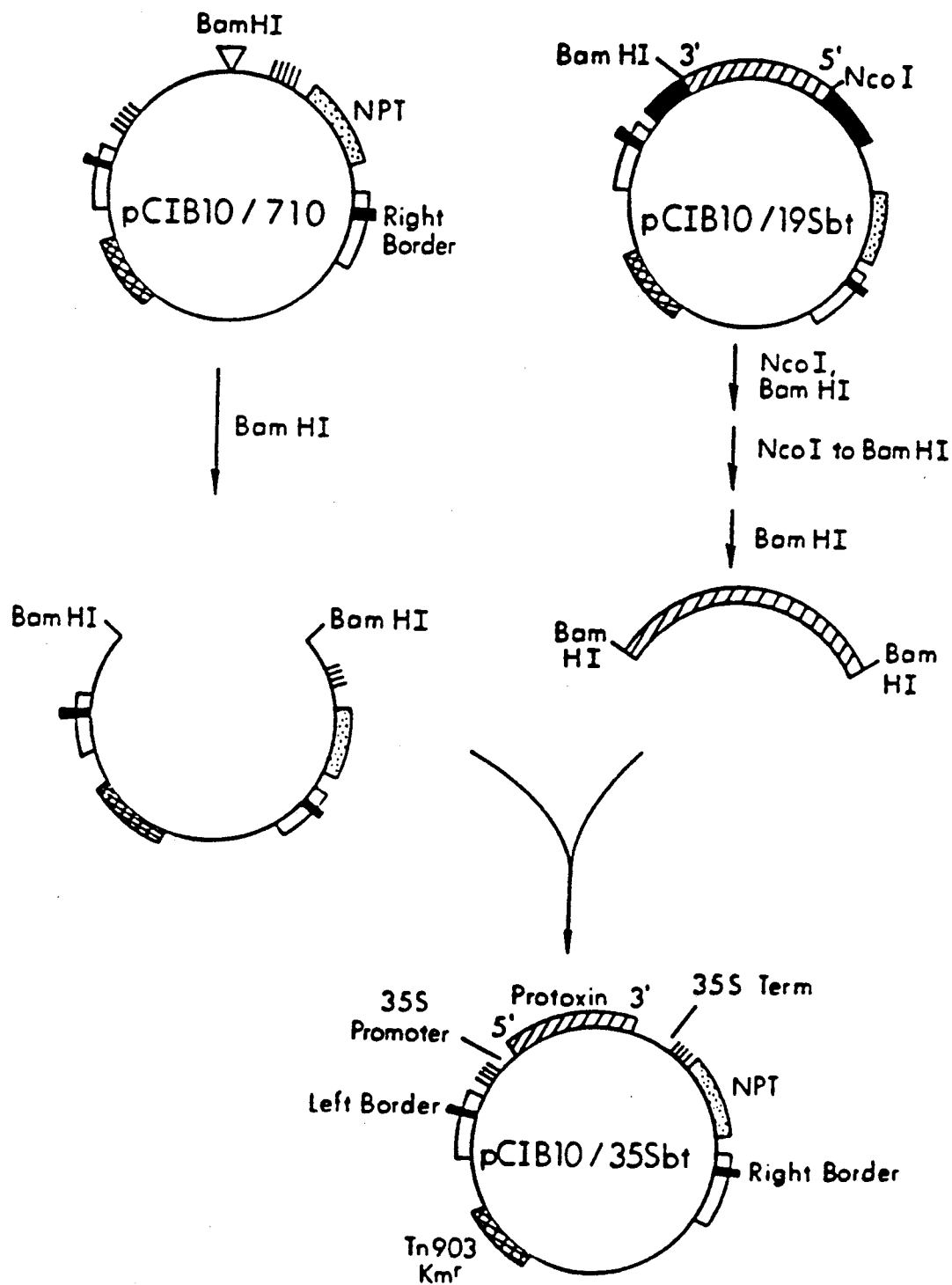
FIG. 29 shows the construction of pCIB10/35Sbt.

In order to transfer plasmid pCIB10/19Sbt from *E. coli* HB101 to Agrobacterium, an intermediate *E. coli* host strain S17-I was used. This strain, obtainable from Agrigenetics Research Corp., Boulder, Co. contains mobilization functions that transfer plasmid pCIB10 directly to Agrobacterium via conjugation, thus avoiding the necessity to transform naked plasmid DNA directly into Agrobacterium (reference for strain S17-1 is Simon et al., "Molecular Genetics of the Bacteria-Plant Interaction", A Puhler, ed, Springer Verlag, Berlin, pages 98–106, 1983, incorporated herein by reference). First, plasmid pCIB10/19Sbt DNA was introduced into calcium chloride-treated S17-1 cells. Next, cultures of transformed S17-1 cells and Agrobacterium tumefaciens strain LBA4404 [Ooms et al., Gene, 14, 33–50 (1981) incorporated herein by reference] were mixed and mated on an N agar (Difco) plate overnight at room temperature. A loopful of the resulting bacteria are streaked onto AB minimal media; Chilton et al., Proc. Natl. Acad. Sci. USA, 77, 7347–7351 (1974), incorporated herein by reference, plated with 50ug/ml kanamycin and incubated at 28° C. Colonies were restreaked onto the same media, then restreaked onto NB agar plates. Slow-growing colonies were picked, restreaked onto AB minimal media with kanamycin and single colonies isolated. This procedure selects for Agrobacteria containing the pCIB10/19SBt plasmid.

Construction of a *Bacillus thuringiensis* protoxin chimeric gene with the CaMV 35S promoter was achieved by construction of a CaMV 35S Promoter Cassette Plasmid pCIB710 was constructed as shown in FIG. 27. This plasmid contained CaMV promoter and transcription termination sequences for the 35S RNA transcript [Covey, S.N., Lomonossoff, G.P. and Hull, R., Nucleic Acids Research vol. 9, 6735–6747 (1981) incorporated herein by reference]. A 1149-bp BglII restriction fragment of CaMV DNA in Hohn et al., Current Topics in Microbiology and Immunology, 96, 194–220 and Appendices A to G (1982) incorporated herein by reference]was isolated from plasmid pLVlll (obtained from Dr. S. Howell Univ. California-San Diego; alternatively, the fragment can be isolated directly from CaMV DNA) by preparative agarose gel electrophoresis as described earlier and mixed with BamHI-cleaved plasmid pUC19 DNA, treated with T4 DNA ligase, and transformed into E. coli. The BamHI restriction site in the resulting plasmid has been destroyed by ligation of the BglII cohesive ends to the BamHI cohesive ends. The resulting plasmid, called pUC19/35S, was then used in oligonucleotide-directed in-vitro mutagensis to insert the BamHI recognition sequence GGATCC immediately following CaMV nucleotide 7483 in the Hohn reference. The resulting plasmid, pCIB710, contains the CaMV 35S promotor region and transcription termination region separated by a BamHI restriction site. DNA sequences inserted into this BamHI site will be expressed in plants by the CaMV transcription regulation sequences. pCIB710 does not contain any ATG translation initiation codons between the start of transcription and the BamHI site.

Insertion of the CaMV 35S promoter/Terminator Cassette into pCIB10 occurred by the steps outlined in FIG. 28. Plasmids pCIB10 and pCIB710 DNAs were digested with EcoRI and SalI, mixed and ligated. The resulting plasmid, pCIB10/710 has the CaMV 35S promoter/terminator cassette inserted into the plant transformation vector pCIB10. The CaMV 35S sequences are between the T-DNA borders in pCIB10, and thus will be inserted into the plant genome in plant transformation.

Insertion of the *Bacillus thuringiensis* protoxin gene into pCIB10/710 occurred by the steps outlined in FIG. 29. As a source of the protoxin gene, plasmid pCIB10/19Sbt was digested with BamHI and NcoI, and the 3.6-kb fragment containing the protoxin gene was isolated by preparative gel electrophoresis. The fragment was then mixed with synthetic NcoI-BamHI adapter with the sequence 5'-CATGGCCGGATCCGGC-3', then digested with BamHI. This step creates BamHI cohesive ends at both ends of the protoxin fragment. This fragment was then inserted into BamHI-cleaved pCIB10/710. The resulting plasmid, pCIB10/35Sbt, shown in FIG. 29, contains the protoxin gene between the CaMV 35S promoter and transcription termination sequences.

Transfer of the plasmid pCIB10/35Sbt into Agrobacterium tumefaciens strain LBA4404 was as described above.

Construction of a deleted *Bacillus thuringiensis* protoxin gene containing approximately 725 amino acids, and construction of a chimeric gene containing this deleted gene with the CaMV 35S promoter was made by removing the COOH-terminal portion of the gene by cleaving at the KpnI restriction endonuclease site at position 2325 in the sequence shown in Formula Plasmid pCIB10/35Sbt (FIG. 29) was digested with BamHI and KpnI, and the approximately 2.2-kbp BamHI/KpnI fragment containing the deleted protoxin gene isolated by preparative agarose gel electrophoresis. To convert the KpnI site at the 3' end to a BamHI site, the fragment was mixed with a KpnI/BamHI adapter oligonucleotide and ligated. This fragment is then mixed with BamHI-cleaved pCIB10/710 (FIG. 28).

Figure 31:
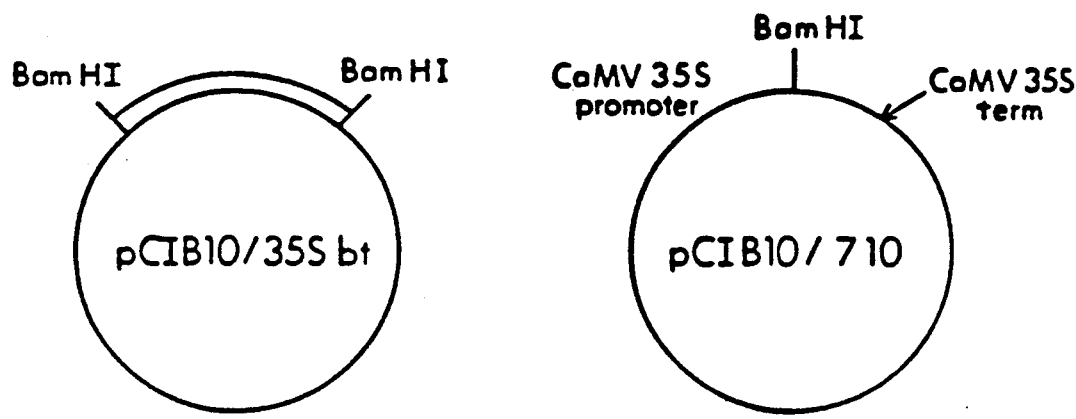
FIG. 31 shows the construction of pCIB10/35Sbt(BclI).
Figure 31:
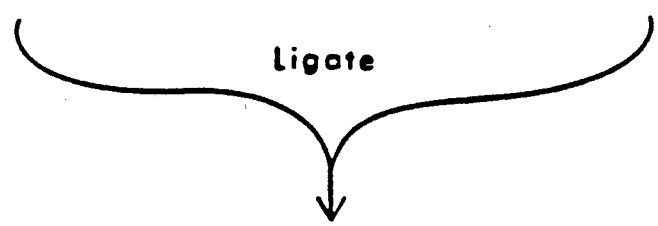
Figure 31:
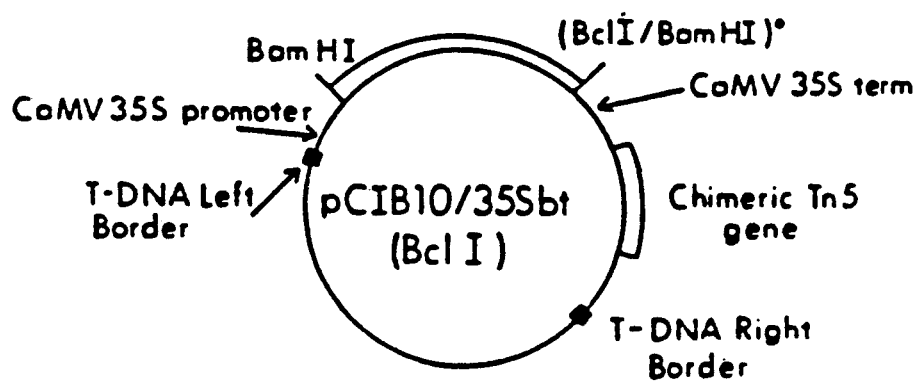

A deleted protoxin gene containing approximately 645 amino acids was made by removing the COOH-terminal portion of the gene by cleaving at the BclI restriction endonuclese site at position 2090 in the sequence shown in Formula 1. Plasmid pCIB10/35Sbt (FIG. 29) was digested with BamHI and BclI, and the approximately 1.9-kbp BamHI/BclI fragment containing the deleted protoxin gene isolated by preparative agarose gel electrophoresis. Since BclI creates a cohesive end compatible with BamHI, no further manipulation is required prior to ligating this fragment into BamHI-cleaved pCIB10/710 (FIG. 28). The resulting plasmid, which has the structure pCIB10/35Sbt(BclI) shown in FIG. 31 was selected on kanamycin.

Figure 30:
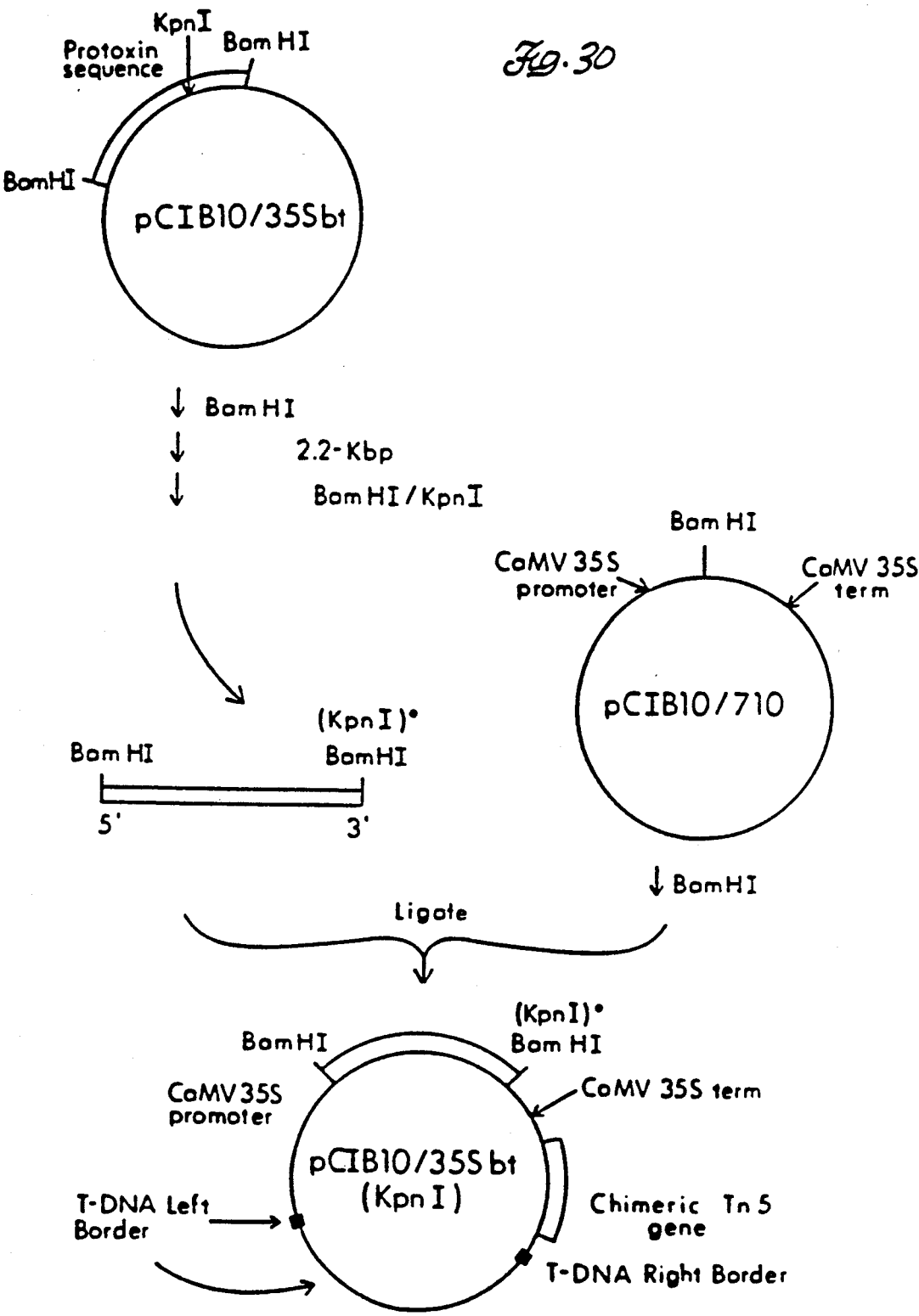
FIG. 30 shows the construction of pCIB10//35Sbt(KpnI).

The resulting transformants, designated pCIB10/35Sbt(KpnI) and shown in FIG. 30, contain the deleted protoxin gene of approximately 725 amino acids. These transformants are selected on kanamycin.

Figure 32:
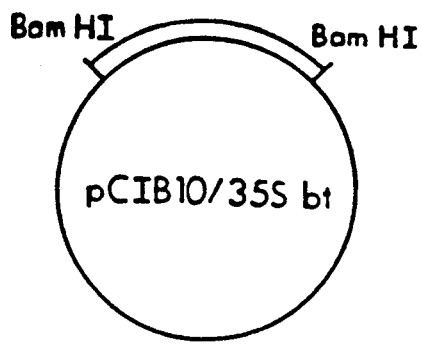
FIG. 32 shows the construction of pCIB10/35Sbt(607)
Figure 32:
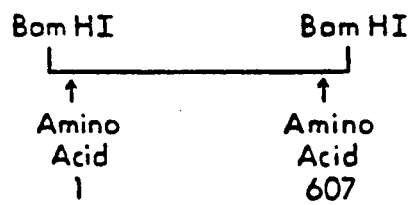
Figure 32:
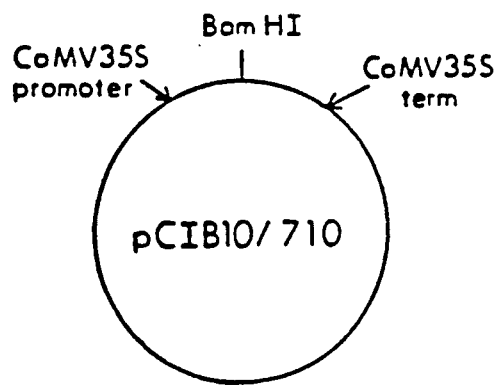
Figure 32:
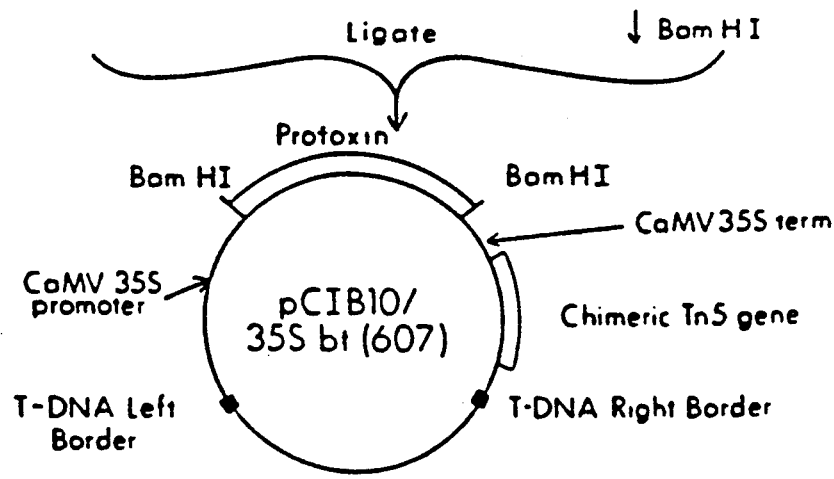

A deleted protoxin gene was made by introducing a BamHI cleavage site (GGATCC). This is done by cloning the BamHI fragment containing the protoxin sequence from pCIB10/35Sbt into mp18, and using standard oligonucleotide mutagensis procedures described above. After mutagensis, double-stranded replicative form DNA is prepared from the M13 clone, which is then digested with BamHI. The approximately 1.9-kbp fragment containing the deleted protoxin gene is inserted into BamHI-cleaved pCIB10/710. The resulting plasmid, which the structure pCIB10/35Sbt(607) shown in FIG. 32 is selected for on kanamycin.

The pCIB10/Sbt 607 was used. Transformation was accomplished as detailed in Example 7 with the change that the 1 ml aliquots were plated immediately on medium containing selective antibiotics. This selection medium contained kanamycin (50 ug/ml) or G418 (25 ug/ml). Expression of the NPT chimeric gene in both transformed plant tissue allows the selection of this tissue on either antibiotic.

In 2–4 weeks, transformed tissue became apparent on the selection plates. Plant material was selected on kanamycin or G418. Plant tissue (either individual embryos or callus) was then extracted with buffer and assayed for expression of the BT gene product by ELISA assay. The conditions of extraction are as follows: per 100mg of tissue, homogenize in 0.1 ml of extraction buffer containing 50 mM NaCO$_3$ (pH9.5), 0.05% Triton, 0.05% Tween, 100nMNaCl, 10mM EDTA, 1mM leupeptine, and 1mM PMSF. The leupeptine and PMSF are added immediately prior to use from 100× stock solutions. The tissue was ground with a motor driven pestle. After extraction, 2M Tris pH7 was added to adjust pH to 8.0–8.5 then centrifuged at 12,000 RPM in a Beckman microfuge 12 (10 minutes at 4° C.), and the supernatant saved for enzyme linked immunosorbent assay ("ELISA").

ELISA techniques as a general tool is described by M. F. Clark et al in *Methods in Enzymology* 118:742–766 (1986), incorporated by reference.

An ELISA for the Bt toxin was developed using standard procedures and used to analyze transgenic plant material for expression of Bt sequences. For this procedure, an ELISA plate is pretreated with ethanol and affinity-purified rabbit anti-Bt antiserum (50 ul) at a concentration of 3 ug/ml in borate-buffered saline (see below) is added to the plate. This was allowed to incubate overnight at 4° C. Antiserum was produced in response to immunizing rabbits with gradient-purified Bt crystals [Ang, B.J. & Nickerson, K.W.; Appl. Environ. Microbiol. 36: 625–626 (1978)], incorporated herein by reference, solubilized with sodium dodecyl sulfate and washed with ELISA Wash Buffer (see below). It was then treated for 1 hour at room temperature with Blocking Buffer (see below) washed with ELISA Wash Buffer. Plant extract was added in an amount to give 50 ug of protein (this is typically ca. 5 microliters of extract). Leaf extraction buffer as protein is determined by the Bradford method [Bradford, M., Anal. Biochem. 72:248 (1976) incorporated herein by reference]using a commercially available kit obtained from Bio-Rad, Richmond, California. If dilution of the leaf extract is necessary, ELISA Diluent (see below)] is used. Allow this to incubate overnight at 4° C. After a wash with ELISA Wash Buffer, 50 ul affinity-purified goat anti-Bt antiserum is added at a concentration of 3 ug/ml protein in ELISA Diluent. This is allowed to incubate for 1 hour at 37° C., then washed with ELISA Wash Buffer. 50 ul rabbit anti-goat antibody bound to alkaline phosphatase [commercially available from Sigma Chemicals, St. Louis, Mo.] is diluted 1:500 in ELISA Diluent and allowed to incubate for 1 hour at 37° C., then washed with ELISA Wash Buffer. 50 microliters substrate [0.6 mg/ml p-nitrophenyl phosphate in, ELISA Substrate Buffer (see below) are added and incubated for 30 minutes at room temperature. Reaction is terminated by adding 50 microliters of 3 M NaOH. Absorbance is read at 405 nm in modified ELISA reader [Hewlett Packard, Stanford, Ca.].

Plant tissue transformed with the pCIB10/35SBt(BclI) when assayed using this ELISA procedure showed a positive reaction, indicating expression of the Bt gene.

| EPBS (ELISA Phosphate Buffered Saline) | | |
|---|---|---|
| 10 mM NaPhosphate: | Na$_2$HPO$_4$ | 4.68 grams/4 liters |
| | NaH$_2$PO$_4$.H2O | 0.976 grams/4 liters |
| 140 mM NaCl | NaCl | 32.7 grams/4 liters | pH should be approximately 7.4.

Borate Buffered Saline 100 mM Boric acid
25 mM Na Borate
75 mM NaCl
Adjust pH to 8.4–8.5 with HCl or NaOH as needed.

ELISA Blocking Buffer

In EPBS,
1% BSA
0.02% Na azide

ELISA Wash Buffer

10mM Tris-HCl pH 8.0

0.05% Tween 20
0.02% Na Azide 2.5M TRIS

ELISA Diluent

In EPBS:
0.05% Tween 20
1% BSA
0.02% Na Azide

ELISA Substrate Buffer

In 500 mls,
48 ml Diethanolamine,
24.5 mg $MgCl_2$;
adjust to pH 9.8 with HCl.

ELISA Substrate 15 mg p-nitrophenyl phosphate in 25 ml Substrate Buffer.

For bioassays, cell suspensions from antibiotic-resistant cell cultures obtained from transformations with these Agrobacteria were initiated. Suspensions were grown in medium supplemented with G418 (25mg/L), and subcultured into fresh antibiotic-containing medium on 7-10 day intervals. Samples of these cultures were then used in bioassays to test for toxicity to lepidopterous insects. Twenty ml aliquots of these cultures were allowed to settle (cell volume =3-4ml), and resuspended in medium lacking antibiotics. Suspensions were then allowed to grow for an additional two days in this medium to deplete the cells of any residual antibiotic. Two circles of wet Whatman 2.3 cm filter paper were placed in the bottom of a ¾ oz portion cup. A layer of transformed suspension culture cells 0.2 cm deep was placed onto the filter paper disk. A newly-hatched *Manduca sexta* or *Heliothis virescens* larva was placed into each portion cup. Controls were made up of larvae fed on non-transformed suspension culture cells. Discs were replenished on 2-day intervals or as needed. Manduca larvae generally require more plant material. The growth rate and mortality of the larvae feeding on transformed cells compared with the growth rate of larvae feeding on untransformed cells was scored after 5 days, and clearly affirmed the toxicity of the BT gene product in transformed cotton cells.

Example 15

*Heliothis virescens* eggs laid on sheets of cheesecloth are obtained from the Tobacco Insect Control Laboratory at North Carolina State University, Raleigh, N. C. The cheesecloth sheets are transferred to a large covered glass beaker and incubated at 29° C. with wet paper towels to maintain humidity. The eggs hatched within three days. As soon as possible after hatching, the larvae (one larva per cup.) are transferred to covered ¾ oz. plastic cups. Each cup contains cotton leaf discs. Larvae are transferred using a fine bristle paint brush.

Leaf discs one centimeter in diameter are punched from leaves of cotton plants and placed on a circle of wet filter paper in the cup with the larva. At least 6-10 leaf discs, representing both young and old leaves, are tested from each plant. Leaf discs are replaced at two-day intervals, or as necessary to feed the larvae. Growth rates [size or combined weight of all replica worms] and mortality of larvae feeding on leaves of transformed plants are compared with those of larva feeding on untransformed cotton leaves.

Larvae feeding on discs of cotton transformed with pCIB10/35SB5(BclI) show a decrease in growth rate and increase in mortality compared with controls.

It was observed that a certain number of our regenerated plants (5-10%) appeared to have acquired genetically heritable phenotypic variations as a consequence of the process of regeneration. This variation is known as somaclonal variation. The following examples illustrate how somaclonal variation as a consequence of our regeneration procedure has been used to introduce commercially useful new traits into cotton varieties.

Example 16

Cotton Regenerants Tolerant to Fungal Pathogens

The procedure of Example 1 was followed, and regenerated cotton plants obtained of the variety SJ5 and SJ4 were hardened and placed in the soil. These plants were self-pollinated and the seed, representing the F1 generation, collected.

Figure 33:
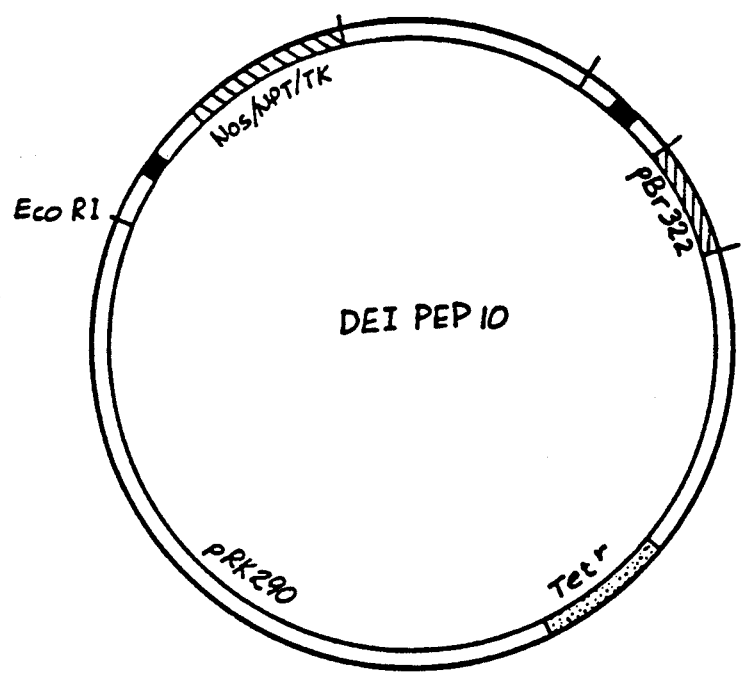
FIG. 33 depicts the vector DEI PEP10.
Figure 34:
FIG. 34 is a photo showing a field trial made up of cotton regenerants planted in a Verticillium infested field.
Figure 35:
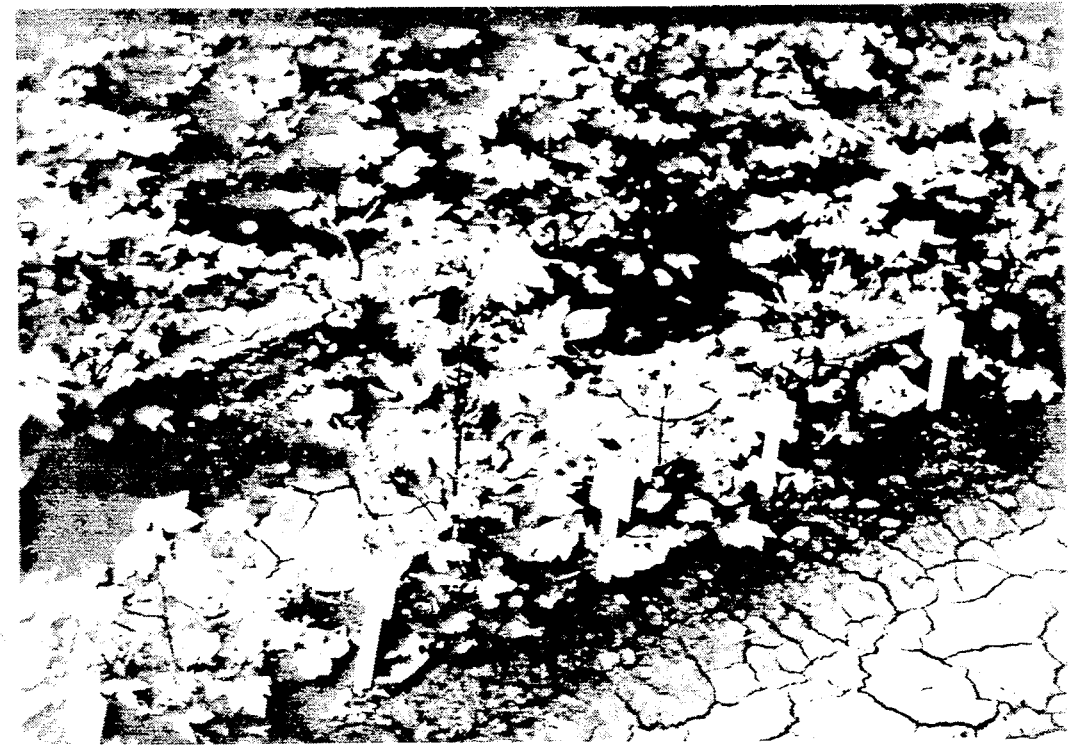
FIG. 35 is a photo showing progeny of a regenerated SJ4 plant in the field trial shown in FIG. 33. A somaclonal variant with improved tolerance to Verticillium fungus is indicated by the arrow.

To obtain regenerants (somaclonal variants) more tolerant to Verticillium, the F1 generation was planted in a Verticillium infested field for progeny row analysis. Seed of the varieties SJ4 and SJ5 were planted in the field as controls. Somaclonal variants more tolerant than the parental varieties to the Verticillium fungus were identified in a few of the progeny rows (5%) by assessing overall plant vigor, yield, and the absence of foliar symtoms associated with the disease. FIG. 33 shows the progeny rows of regenerants planted in a Verticillium infested field. FIG. 34 shows a Verticillium tolerant somaclonal variant of variety SJ4. This improvement in tolerance to the fungal pathogen was found to be genetically stable and passed on to subsequent generations.

Example 17

The procedure of Example 13 was followed except that, rather than planting in disease-infested soil, the F1 generation was planted in a cotton breeding nursery. The overall growth habit of the F1 regenerated progeny was compared to that of the control varieties. Somaclonal variants were identified which were more uniform in growth habit and shorter in stature than the parental variety. One SJ5 regenerant, identified in our trials as Phy 6, was 20% shorter in stature than the parental variety. This kind of growth habit is desireable in cotton grown under narrow row (30" row spacing) cultural conditions. These traits were found to be genetically stable and passed on to subsequent generations.

Example 18

Cotton regenerants with improved fiber traits

The procedure of Example 13 was followed except that the F1 progeny of regenerants were planted in a cotton breeding nursery and allowed to set fruit. When the bolls were mature, the cotton was harvested and subjected to an analysis of several fiber quality traits including length, uniformity, tensile strength, elasticity, and micronaire. Somaclonal variants were identified which were improved significantly over the parental variety in one or more of these traits. Representative data from F2 progeny (self pollination of the F1) are included in the following Table 1. Values marked with an asterisk represent improvements in SJ5 regenerants which are statistically significant and have been found to breed true in subsequent generations.

TABLE 1

| Variety or strain | Fiber Properties | | | | |
|---|---|---|---|---|---|
| | Length | Uniformity Index | Tensile Strength | Elasticity | Micronaire |
| SJ5 | 1.13 | 48.7 | 24.7 | 6.8 | 4.27 |
| 3SP16 | 1.27* | 51.2 | 24.6 | 8.0* | 4.10* |
| 3SP20 | 1.28* | 53.1* | 23.1 | 7.6* | 4.13* |
| 5SP10 | 1.11 | 53.2* | 25.7* | 6.2 | 4.55 |
| 5SP17 | 1.18 | 51.7 | 26.7* | 7.1 | 4.43 |

Example 19

Cotton regenerants with improved yield

The procedure of Example 13 was followed except that the F1 progeny of regenerants of the variety SJ4 were planted in replicated yield trials along with non-regenerated controls. One variant, which exhibited a more uniform growth habit and more vigorous growth habit, yielded 4% more cotton than the parental variety in the same trial. The data are given in Table 2 below.

TABLE 2

| Variety or Strain | X̄ Yield per plot (lb) | X̄ Yield lbs/Acre | % Increase |
|---|---|---|---|
| SJ4 Control | 28.0 | 3049 | |
| Phy 4 | 29.1 | 3169 | 4%* |

*This difference was significant at the 95% confidence level.

A 4% increase in yield would represent a return of almost $20 per acre to the average cotton grower in California, where over one million acres of cotton are grown annually.

Example 20

Cotton Regenerants tolerant to a herbicide (kanamycin)

Suspension cultures of the cotton variety B1644 were developed according to the method of Example 5. Suspension cultures were then plated onto an agar medium as descried in Example 6, but supplemented with the herbicide (antibiotic) kanamycin (25mg/l). Most of the cells in the population died, but a few (1 to 5%) were tolerant and survived. These were selectively subcultured onto agar-solidified media supplemented with increasing concentrations of kanamycin, until the final concentration reached 50mg/l. Embryos were then developed from this callus, and those resistant embryos were germinated into kanamycin resistant plants.

FORMULA I

| 10 | 20 | 30 | 40 | 50 | 60 |
|---|---|---|---|---|---|
| GTTAACACCC | TGGGTCAAAA | ATTGATATTT | AGTAAAATTA | GTTGCACTTT | GTGCATTTTT |
| 70 | 80 | 90 | 100 | 110 | 120 |
| TCATAAGATG | AGTCATATGT | TTTAAATTGT | AGTAATGAAA | AACAGTATTA | TATCATAATG |
| 130 | 140 | 150 | 160 | 170 | 180 |
| AATTGGTATC | TTAATAAAAG | AGATGGAGGT | AACTTATGGA | TAACAATCCG | AACATCAATG |
| 190 | 200 | 210 | 220 | 230 | 240 |
| AATGCATTCC | TTATAATTGT | TTAAGTAACC | CTGAAGTAGA | AGTATTAGGT | GGAGAAAGAA |
| 250 | 260 | 270 | 280 | 290 | 300 |
| TAGAAACTGG | TTACACCCCA | ATCGATATTT | CCTTGTCGCT | AACGCAATTT | CTTTTGAGTG |
| 310 | 320 | 330 | 340 | 350 | 360 |
| AATTTGTTCC | CGGTGCTGGA | TTTGTGTTAG | GACTAGTTGA | TATAATATGG | GGAATTTTTG |
| 370 | 380 | 390 | 400 | 410 | 420 |
| GTCCCTCTCA | ATGGGACGCA | TTTCCTGTAC | AAATTGAACA | GTTAATTAAC | CAAAGAATAG |
| 430 | 440 | 450 | 460 | 470 | 480 |
| AAGAATTCGC | TAGGAACCAA | GCCATTTCTA | GATTAGAAGG | ACTAAGCAAT | CTTTATCAAA |
| 490 | 500 | 510 | 520 | 530 | 540 |
| TTTACGCAGA | ATCTTTTAGA | GAGTGGGAAG | CAGATCCTAC | TAATCCAGCA | TTAAGAGAAG |
| 550 | 560 | 570 | 580 | 590 | 600 |
| AGATGCGTAT | TCAATTCAAT | GACATGAACA | GTGCCCTTAC | AACCGCTATT | CCTCTTTTTG |
| 610 | 620 | 630 | 640 | 650 | 660 |
| CAGTTCAAAA | TTATCAAGTT | CCTCTTTTAT | CAGTATATGT | TCAAGCTGCA | AATTTACATT |
| 670 | 680 | 690 | 700 | 710 | 720 |
| TATCAGTTTT | GAGAGATGTT | TCAGTGTTTG | GACAAAGGTG | GGGATTTGAT | GCCGCGACTA |
| 730 | 740 | 750 | 760 | 770 | 780 |
| TCAATAGTCG | TTATAATGAT | TTAACTAGGC | TTATTGGCAA | CTATACAGAT | CATGCTGTAC |
| 790 | 800 | 810 | 820 | 830 | 840 |
| GCTGGTACAA | TACGGGATTA | GAGCGTGTAT | GGGGACCGGA | TTCTAGAGAT | TGGATAAGAT |
| 850 | 860 | 870 | 880 | 890 | 900 |
| ATAATCAATT | TAGAAGAGAA | TTAACACTAA | CTGTATTAGA | TATCGTTTCT | CTATTTCCGA |
| 910 | 920 | 930 | 940 | 950 | 960 |
| ACTATGATAG | TAGAACGTAT | CCAATTCGAA | CAGTTTCCCA | ATTAACAAGA | GAAATTTATA |
| 970 | 980 | 990 | 1000 | 1010 | 1020 |
| CAAACCCAGT | ATTAGAAAAT | TTTGATGGTA | GTTTTCGAGG | CTCGGCTCAG | GGCATAGAAG |
| 1030 | 1040 | 1050 | 1060 | 1070 | 1080 |
| GAAGTATTAG | GAGTCCACAT | TTGATGGATA | TACTTAACAG | TATAACCATC | TATACGGATG |
| 1090 | 1100 | 1110 | 1120 | 1130 | 1140 |
| CTCATAGAGG | AGAATATTAT | TGGTCAGGGC | ATCAAATAAT | GGCTTCTCCT | GTAGGGTTTT |
| 1150 | 1160 | 1170 | 1180 | 1190 | 1200 |
| CGGGGCCAGA | ATTCACTTTT | CCGCTATATG | GAACTATGGG | AAATGCAGCT | CCACAACAAC |
| 1210 | 1220 | 1230 | 1240 | 1250 | 1260 |
| GAATTGTTGC | TCAACTAGGT | CAGGGCGTGT | ATAGAACATT | ATCGTCCACT | TTATGTAGAA |
| 1270 | 1280 | 1290 | 1300 | 1310 | 1320 |
| GACCTTTTAA | TATAGGGATA | AATAATCAAC | AACTATCTGT | TCTTGACGGG | ACAGAATTTG |
| 1330 | 1340 | 1350 | 1360 | 1370 | 1380 |
| CTTATGGAAC | CTCCTCAAAT | TTGCCATCCG | CTGTATACAG | AAAAAGCGGA | ACGGTAGATT |
| 1390 | 1400 | 1410 | 1420 | 1430 | 1440 |

FORMULA I

| | | | | | |
|---|---|---|---|---|---|
| CGCTGGATGA 1450 | AATACCGCCA 1460 | CAGAATAACA 1470 | ACGTGCCACC 1480 | TAGGCAAGGA 1490 | TTTAGTCATC 1500 |
| GATTAAGCCA 1510 | TGTTTCAATG 1520 | TTTCGTTCAG 1530 | GCTTTAGTAA 1540 | TAGTAGTGTA 1550 | AGTATAATAA 1560 |
| GAGCTCCTAT 1570 | GTTCTCTTGG 1580 | ATACATCGTA 1590 | GTGCTGAATT 1600 | TAATAATATA 1610 | ATTCCTTCAT 1620 |
| CACAAATTAC 1630 | ACAAATACCT 1640 | TTAACAAAAT 1650 | CTACTAATCT 1660 | TGGCTCTGGA 1670 | ACTTCTGTCG 1680 |
| TTAAAGGACC 1690 | AGGATTTACA 1700 | GGAGGAGATA 1710 | TTCTTCGAAG 1720 | AACTTCACCT 1730 | GGCCAGATTT 1740 |
| CAACCTTAAG 1750 | AGTAAATATT 1760 | ACTGCACCAT 1770 | TATCACAAAG 1780 | ATATCGGGTA 1790 | AGAATTCGCT 1800 |
| ACGCTTCTAC 1810 | CACAAATTTA 1820 | CAATTCCATA 1830 | CATCAATTGA 1840 | CGGAAGACCT 1850 | ATTAATCAGG 1860 |
| GGAATTTTTC 1870 | AGCAACTATG 1880 | AGTAGTGGGA 1890 | GTAATTTACA 1900 | GTCCGGAAGC 1910 | TTTAGGACTG 1920 |
| TAGGTTTTAC 1930 | TACTCCGTTT 1940 | AACTTTTCAA 1950 | ATGGATCAAG 1960 | TGTATTTACG 1970 | TTAAGTGCTC 1980 |
| ATGTCTTCAA 1990 | TTCAGCAAT 2000 | GAAGTTTATA 2010 | TAGATCGAAT 2020 | TGAATTTGTT 2030 | CCGGCAGAAG 2040 |
| TAACCTTTGA 2050 | GGCAGAATAT 2060 | GATTTAGAAT 2070 | GAGCACAAAA 2080 | GGCGGTGAAT 2090 | GAGCTGTTTA 2100 |
| CTTCTTCCAA 2110 | TCAAATCGGG 2120 | TTAAAAACAG 2130 | ATGTGACGGA 2140 | TTATCATATT 2150 | GATCAAGTAT 2160 |
| CCAATTTAGT 2170 | TGAGTGTTTA 2180 | TCTGATGAAT 2190 | TTTGTCTGGA 2200 | TGAAAAAAAA 2210 | GAATTGTCCG 2220 |
| AGAAAGTCAA 2230 | ACATGCGAAG 2240 | CGACTTAGTG 2250 | ATGAGCGGAA 2260 | TTTACTTCAA 2270 | GATCCAAACT 2280 |
| TTAGAGGGAT 2290 | CAATAGAGAA 2300 | CTAGACCGTG 2310 | GCTGGAGAGG 2320 | AAGTACGGAT 2330 | ATTACCATCC 2340 |
| AAGGAGGCGA 2350 | TGACGTATTC 2360 | AAAGAGAATT 2370 | ACGTTACGCT 2380 | ATTGGGTACC 2390 | TTTGATGAGT 2400 |
| GCTATCCAAC 2410 | GTATTTATAT 2420 | CAAAAAATAG 2430 | ATGAGTCGAA 2440 | ATTAAAGCC 2450 | TATACCCGTT 2460 |
| ACCAATTAAG 2470 | AGGGTATATC 2480 | GAAGATAGTC 2490 | AAGACTTAGA 2500 | AATCTATTTA 2510 | ATTCGCTACA 2520 |
| ATGCCAAACA 2530 | CGAAACAGTA 2540 | AATGTGCCAG 2550 | GTACGGGTTC 2560 | CTTATGGCCG 2570 | CTTTCAGCCC 2580 |
| CAAGTCCAAT 2590 | CGGAAAATGT 2600 | GCCCATCATT 2610 | CCCATCATTT 2620 | CTCCTTGGAC 2630 | ATTGATGTTG 2640 |
| GATGTACAGA 2650 | CTTAAATGAG 2660 | GACTTAGGTG 2670 | TATGGGTGAT 2680 | ATTCAAGATT 2690 | AAGACGCAAG 2700 |
| ATGGCCATGC 2710 | AAGACTAGGA 2720 | AATCTAGAAT 2730 | TTCTCGAAGA 2740 | GAAACCATTA 2750 | GTAGGAGAAG 2760 |
| CACTAGCTCG 2770 | TGTGAAAAGA 2780 | GCGGAGAAAA 2790 | AATGGAGAGA 2800 | CAAACGTGAA 2810 | AAATTGGAAT 2820 |
| GGGAAACAAA 2830 | TATTGTTTAT 2840 | AAAGAGGCAA 2850 | AAGAATCTGT 2860 | AGATGCTTTA 2870 | TTTGTAAACT 2880 |
| CTCAATATGA 2890 | TAGATTACAA 2900 | GCGGATACCA 2910 | ACATCGCGAT 2920 | GATTCATGCG 2930 | GCAGATAAAC 2940 |
| GCGTTCATAG 2950 | CATTCGAGAA 2960 | GCTTATCTGC 2970 | CTGAGCTGTC 2980 | TGTGATTCCG 2990 | GGTGTCAATG 3000 |
| CGGCTATTTT 3010 | TGAAGAATTA 3020 | GAAGGGCGTA 3030 | TTTTCACTGC 3040 | ATTCTCCCTA 3050 | TATGATGCGA 3060 |
| GAAATGTCAT 3070 | TAAAAATGGT 3080 | GATTTTAATA 3090 | ATGGCTTATC 3100 | CTGCTGGAAC 3110 | GTGAAAGGGC 3120 |
| ATGTAGATGT 3130 | AGAAGAACAA 2140 | AACAACCACC 3150 | GTTCGGTCCT 3160 | TGTTGTTCCG 3170 | GAATGGGAAG 3180 |
| CAGAAGTGTC 3190 | ACAAGAAGTT 3200 | CGTGTCTGTC 3210 | CGGGTCGTGG 3220 | CTATATCCTT 3230 | CGTGTCACAG 3240 |
| CGTACAAGGA 3250 | GGGATATGGA 3260 | GAAGGTTGCG 3270 | TAACCATTCA 3280 | TGAGATCGAG 3290 | AACAATACAG 3300 |
| ACGAACTGAA 3310 | GTTTAGCAAC 3320 | TGTGTACAAG 3330 | AGGAAGTATA 3340 | TCCAAACAAC 3350 | ACGGTAACGT 3360 |
| GTAATGATTA 3370 | TACTGCGACT 3380 | CAAGAAGAAT 3390 | ATGAGGGTAC 3400 | GTACACTTCT 3410 | CGTAATCGAG 3420 |
| GATATGACGG 3430 | AGCCTATGAA 3440 | AGCAATTCTT 3450 | CTGTACCAGC 3460 | TGATTATGCA 3470 | TCAGCCTATG 3480 |
| AAGAAAAAGC 3490 | ATATACAGAT 3500 | GGACGAAGAG 3510 | ACAATCCTTG 3520 | TGAATCTAAC 3530 | AGAGGATATG 3540 |
| GGGATTACAC 3550 | ACCACTACCA 3560 | GCTGGCTATG 3570 | TGACAAAAGA 3580 | ATTAGAGTAC 3590 | TTCCCAGAAA 3600 |
| CCGATAAGGT 3610 | ATGGATTGAG 3620 | ATCGGAGAAA 3630 | CGGAAGGAAC 3640 | ATTCAACGTG 3650 | GACAGCGTGG 3660 |
| AATTACTTCT 3670 | TATGGAGGAA 3680 | TAATATATGC 3690 | TTTATAATGT 3700 | AAGGTGTGCA 3710 | AATAAAGAAT 3720 |
| GATTACTGAC 3730 | TTGTATTGAC 3740 | AGATAAATAA 3750 | GGAAATTTTT 3760 | ATATGAATAA 3770 | AAAACGGGCA 3780 |
| TCACTCTTAA 3790 | AAGAATGATG 3800 | TCCGTTTTTT 3810 | GTATGATTTA 3820 | ACGAGTGATA 3830 | TTTAAATGTT 3840 |
| TTTTTTGCGA | AGGCTTTACT | TAACGGGGTA | CCGCCACATG | CCCATCAACT | TAAGAATTTG |

-continued

FORMULA I

| 3850 | 3860 | 3870 | 3880 | 3890 | 3900 |
|---|---|---|---|---|---|
| CACTACCCCC | AAGTGTCAAA | AAACGTTATT | CTTTCTAAAA | AGCTAGCTAG | AAAGGATGAC |
| 3910 | 3920 | 3930 | 3940 | 3950 | 3960 |
| ATTTTTTATG | AATCTTTCAA | TTCAAGATGA | ATTACAACTA | TTTTCTGGAG | AGCTGTATCG |
| 3970 | 3980 | 3990 | 4000 | 4010 | 4020 |
| TCATTTAACC | CCTTCTCTTT | TGGAAGAACT | CGCTAAAGAA | TTAGGTTTTG | TAAAAAGAAA |
| 4030 | 4040 | 4050 | 4060 | 4070 | 4080 |
| ACGAAAGTTT | TCAGGAAATG | AATTAGCTAC | CATATGTATC | TGGGGCAGTC | AACGTACAGC |
| 4090 | 4100 | 4110 | 4120 | 4130 | 4140 |
| GAGTGATTCT | CTCGTTCGAC | TATGCAGTCA | ATTACACGCC | GCCACAGCAC | TCTTATGAGT |
| 4150 | 4160 | 4170 | 4180 | 4190 | 4200 |
| CCAGAAGGAC | TCAATAAACG | CTTTGATAAA | AAAGCGGTTG | AATTTTTGAA | ATATATTTTT |
| 4210 | 4220 | 4230 | 4240 | 4250 | 4260 |
| TCTGCATTAT | GGAAAAGTAA | ACTTTGTAAA | ACATCAGCCA | TTTCAAGTGC | AGCACTCACG |
| 4270 | 4280 | 4290 | 4300 | 4310 | 4320 |
| TATTTTCAAC | GAATCCGTAT | TTTAGATGCG | ACGATTTTCC | AAGTACCGAA | ACATTTAGCA |
| 4330 | 4340 | 4350 | 4360 | | |
| CATGTATATC | CTGGGTCAGG | TGGTTGTGCA | CAAACTGCAG | | |

What is claimed is:

1. A method for the regeneration of a cotton plant from somatic cells which comprises the steps of:
   (a) providing a cotton explant which is an immature zygotic embryo or an explant selected from the group consisting of hypocotyl, cotyledon and mixtures thereof from a cotton seedling;
   (b) culturing the explant in a first solid callus growth medium which is a full or half-strength Murashige and Skoog growth medium containing glucose as the carbon source supplemented with thiamine hydrochloride, naphthaleneacetic acid and kinetin and inositol at a temperature of from about 25° to about 35° C. under a light-dark cycle of about 16 hours of light at a light intensity of about 2,000 to about 4,000 lux followed by about 8 hours of darkness, said light-dark cycle and changing of the medium being repeated for a period of time sufficient for phenolic secretion from the explant to end, to enable undifferentiated callus to form from the explant;
   (c) transferring the callus from the first solid callus growth medium to a second solid callus growth medium which is full or half strength Murashige and Skoog growth medium comprising sucrose as the carbon source and from about 1 to about 10 mg/l of naphthaleneacetic acid and culturing the callus at a temperature from about 25° to 35° C. under a light-dark cycle of about 16 hours light at a light intensity of about 2,000 to about 4,000 lux followed by about 8 hours of darkness, said light-dark cycle being repeated for a time sufficient to form yellow and white embryogenic callus;
   (d) further subculturing the embryogenic callus to develop to callus containing somatic embryos; and
   (e) transferring somatic embryos to an embryo germination medium which is a Beasley and Ting's medium containing up to about 500 mg/l casein hydrolysate and up to about 1200 mg/l ammonium nitrate and growing the embryos in the embryo germination medium to plantlets sufficiently developed for transfer to soil; and
   (f) transferring the plantlets from the embryo germination medium to soil.

2. The method as claimed in claim 1, in which the explant is from a cotton seedling developed by:
   a) sterilizing cotton seed in a first sterilizing solution;
   b) rinsing the seed in sterile water;
   c) sterilizing the seed in a second sterilizing solution;
   f) rinsing the second sterilization solution from the seed with sterile water;
   g) transferring the seed to a seed germination medium; and
   h) growing the seed in the seed germination medium in the dark for a period of time sufficient to produce a seedling; and
   i) excising the explant from the seedling.

3. The method as defined in claim 2 in which the first sterilizing solution is an aqueous solution containing about 95% by volume ethanol and the second sterilizing solution is an aqueous solution containing about .15% by weight sodium hypochlorite.

4. A method as claimed in claim 2 in which the seed germination medium is a basal agar medium and growth of the seedling in the basal agar medium prior to excising the explant is up to about 4 weeks.

5. A method as claimed in claim 1 in which the light intensity during the hours of light is about 3,000 to about 4,000 lux.

6. A method as claimed in claim 1 wherein once phenolic secretions end the explant is transferred to the second solid callus growth medium and the second solid callus growth medium is changed to a fresh second solid callus growth medium at about 3 to about 4 week intervals.

7. A method as claimed in claim 1 further including the step of transferring the plantlet to soil under conditions of high humidity for a time sufficient for the plantlet to mature to a stage sufficient to enable its transfer to a hot house or field for growth to final maturity.

8. A method as claimed in claim 1 in which the first callus growth medium is a Murashige and Skoog growth medium containing about 0.4 mg/l thiamine hydrochloride, about 30 g/l glucose, about 2 mg/l naphthaleneacetic acid, about 1 mg/l kinetin and about 100 mg/l inositol.

9. A method as claimed in claim 1 in which the second callus growth medium contains from about 1 to about 5 mg/l naphthaleneacetic acid and from 0 to about 1 mg/l cytokinin.

10. A method as claimed in claim 8 in which the second callus growth medium contains from about 1 to about 5 mg/l naphthaleneacetic acid and from 0 to about 1 mg/l cytokinin.

11. A method as claimed in claim 1 in which the first callus growth medium is changed about every 10 days while phenolics are secreted from the explant, and thereafter including sucrose in the second solid callus growth medium as the primary carbon source.

12. A method as claimed in claim 1 in which the first callus growth medium is changed about every ten days while phenolics are secreted from explant, and thereafter including sucrose in the second solid callus growth medium as the primary carbon source.

13. A method for the regeneration of cotton plants from somatic cells, said method comprising the steps of:
   (a) sterilizing at least one cotton seed in a solution containing 95% by volume ethanol for a period of approximately 2-3 minutes;
   (b) rinsing the seed in sterile water;
   (c) soaking the seed in a solution of sodium hypochlorite containing about 15% by weight sodium hypochlorite for a period of from about 15 to about 20 minutes;
   (d) rinsing the seed in sterile water;
   (e) germinating the seed in a dark environment on modified basal agar medium selected from the group consisting of White's medium and half strength Murashige and Skoog medium for a period of up to about 14 days to produce a seedling;
   (f) excising at least one segment selected from the group consisting of hypocotyl, cotyledon or mixtures thereof from the seedling;
   (g) culturing the excised segment on first solid callus growth medium which is a Murashige and Skoog medium supplemented with about 0.4 mg/l thiamine hydrochloride, about 3 g/l glucose, about 2 mg/l naphthaleneacetic acid, about 1 mg/l kinetin and about 100 mg/l inositol in an environment of a temperature of from 25° to 30° C. under a light-dark cycle of 16 hours of light followed by about 8 hours of darkness, at about 3,000 to 4,000 lux light intensity during the hours of light during which the medium is replaced by fresh first solid callus growth medium about every 10 days, said light-dark cycle with changes of the medium being repeated until phenolic secretions from the excised segment end, to enable formation of undifferentiated callus from the explant;
   (h) transferring the callus onto a Murashige and Skoog medium comprising sucrose and about 2 mg/l naphthaleneacetic acid and about 1 mg/l cytokinetin;
   (i) culturing the callus over a period of about three to four months to produce at least one embryo;
   (j) transferring the embryo to a Beasley and Ting's medium comprising up to about 500 mg/l casein hydrolysate, and containing up to about 1,200 mg/l ammonium nitrate and culturing the embryo for a period of about 2 to about 3 months, to produce a plantlet; and
   (k) transferring the plantlet to soil and incubating the plantlet in high humidity to form a plant.

14. The method as defined in claim 13 including the steps of self-pollinating the plant formed from the plantlet to produce seeds and germinating the seeds to produce seedlings.

15. A method for the regeneration of a cotton plant from somatic cotton cells of Acala cotton which comprises steps of:
   (a) providing a cotton explant which is an immature zygotic embryo or an explant selected from the group consisting of hypocotyl, cotyledon and mixtures thereof from the Acala cotton seedling;
   (b) culturing the cotton explant in a first solid callus growth medium which is a full or half-strength Murashige and Skoog growth medium supplemented with thiamine hydrochloride, naphthaleneacetic acid and kinetin and inositol and containing glucose as a carbon source in an environment temperature of from about 25° to about 35° C. under a light-dark cycle of 16 hours of light at about 2,000 to 4,000 lux light intensity followed by about 8 hours of darkness, said light-dark cycle and changing of the medium being repeated for a period of time sufficient for phenolic secretions from the explant to end to enable undifferentiated callus to develop from the explant;
   (c) transferring the callus when phenolic secretions end to a second solid callus growth medium which is selected from group consisting of full strength Murashige and Skoog and half strength Murashige and Skoog growth medium comprising sucrose as the carbon source and from about 1 to about 10 mg/l of naphthaleneacetic acid;
   (d) culturing the callus on the second solid callus growth medium at a temperature of from 25° to 35° C. under a light-dark cycle of 16 hours of light at about 2,000 to 4,000 lux light intensity followed by about 8 hours of darkness, said light-dark cycle being repeated for a period of time sufficient to form yellow to white embryogenic callus providing at least one embryo;
   (e) further subculturing the embryogenic callus to develop callus containing somatic embryos;
   (f) transferring somatic embryos to a plant germination medium which is a Beasley and Ting's medium containing up to about 500 mg/l casein hydrolysate and up to about 1200 mg/l ammonium nitrate;
   (g) culturing the embryo on the plant germination medium for a period of time sufficient to develop a plantlet from the embryo; and
   (h) transferring the plantlets from the embryo germination medium to soil.

16. A method for the regeneration of a cotton plant from somatic cells which comprises the steps of:
   (a) providing an explant which is an immature zygotic embryo or an explant selected from the group consisting of hypocotyl, cotyledon and mixtures thereof derived from a cotton seedling;
   (b) culturing the explant in a first solid callus growth medium which is a Murashige and Skoog growth medium supplemented with thiamine hydrochloride, glucose, naphthaleneacetic acid, kinetin and inositol at a temperature of from about 25° to about 35° C. under a light-dark cycle of about 16 hours light at a light intensity of about 2,000 to about 4,000 lux followed by a darkness cycle about 8 hours of darkness, said light-dark cycle and changing of the medium being repeated for a period of time sufficient for phenolic secretion from the explant to end to enable undifferentiated callus to form from the explant;
   (c) transferring the callus from the first callus growth medium when phenolic secretions end to a second callus growth medium which is a Murashige and Skoog growth medium containing sucrose and from about 1 to about 10 mg/l of naphthaleneacetic acid and culturing the callus at a temperature from about 25° to about 35° C. under a light-dark cycle of about 16 hours of light at a light intensity of about 2,000 to about 4,000 lux followed by about 8 hours of darkness, said light-dark cycle being repeated for a time sufficient to develop embryogenic callus;

(d) suspending parts of the embryogenic callus in fresh liquid second callus growth medium at a concentration from about 750 to about 1,000 mg of callus parts per 8 ml of said liquid second callus growth medium which is a Murashige and Skoog growth medium containing sucrose and from about 1 to about 10 mg/l of naphthaleneacetic acid and culturing the suspended callus at a temperature from about 25° to 35° C. under a light-dark cycle of about 16 hours of light at a light intensity of about 2,000 to about 4,000 lux followed by about 8 hours of darkness, said light-dark cycle being repeated for a time sufficient to develop embryogenic callus; and allowing the suspended parts to grow for a time sufficient to develop embryogenic clumps of a size greater than about 600 microns;

(e) separating the embryogenic clumps greater than about 600 microns from clumps less than about 600 microns; and (f) transferring the embryogenic clumps of a size greater than 600 microns to a plant germination medium which is a Beasley and Ting's medium containing up to about 500 mg/l casein hydrolysate and up to about 1,200 mg/l ammonium nitrate and growing the embryogenic clumps to plantlets.

17. A method for the regeneration of a cotton plant from somatic cells of Acala cotton which comprises the steps of:

(a) providing an explant which is an immature zygotic embryo or an explant selected from the group consisting of hypocotyl, cotyledon and mixtures thereof derived from an Acala cotton seedling;

(b) culturing the explant in a first solid callus growth medium which is a Murashige and Skoog growth medium supplemented with thiamine hydrochloride, glucose, naphthaleneacetic acid, kinetin and inositol at a temperature of from about 25° to about 35° C. under a light-dark cycle of about 16 hours light at a light intensity of about 2,000 to about 4,000 lux followed by a darkness cycle about 8 hours of darkness, said light-dark cycle and changing of the medium being repeated for a period of time sufficient for phenolic secretion from the explant to end to enable undifferentiated callus to form from the explant;

(c) transferring the callus from the first callus growth medium when phenolic secretions end to a second callus growth medium which is a Murashige and Skoog growth medium containing sucrose and from about 1 to about 10 mg/l of naphthaleneacetic acid and culturing the callus at a temperature from about 25° to about 35° C. under a light-dark cycle of about 16 hours of light at a light intensity of about 2,000 to about 4,000 lux followed by about 8 hours of darkness, said light-dark cycle being repeated for a time sufficient to develop embryogenic callus;

(d) suspending parts of the embryogenic callus in fresh liquid second callus growth medium at a concentration from about 750 to about 1,000 mg of callus parts per 8 ml of said liquid second callus growth medium which is a Murashige and Skoog growth medium containing sucrose and from about 1 to about 10 mg/l of naphthaleneacetic acid and culturing the suspended callus at a temperature from about 25° to 35° C. under a light-dark cycle of about 16 hours of light at a light intensity of about 2,000 to about 4,000 lux followed by about 8 hours of darkness, said light-dark cycle being repeated for a time sufficient to develop embryogenic callus; and allowing the suspended parts to grow for a time sufficient to develop embryogenic clumps of a size greater than about 600 microns;

(e) separating the embryogenic clumps greater than about 600 microns from clumps less than about 600 microns; and (f) transferring the embryogenic clumps of a size greater than 600 microns to a plant germination medium which is a Beasley and Ting's medium containing up to about 500 mg/l casein hydrolysate and up to about 1200 mg/l ammonium nitrate and growing the embryogenic clumps to plantlets.

18. A method as claimed in claim 16 in which the clumps of a size less than 600 microns are resuspended in fresh second callus growth medium for further growth of embryogenic clumps.

19. A method as claimed in claim 16 in which the explant is obtained by:
  a) sterilizing of the seed in a first-sterilized solution;
  b) rinsing the seed with sterile water;
  c) sterilizing the seed in a second sterilizing solution;
  d) rinsing the second sterilization solution from the seed with sterile water;
  e) transferring the sterilized seed to a seed germination medium;
  f) culturing the seed in the seed germination medium in the dark for a period of time sufficient to form cotton seedling; and
  g) excising the explant from the cotton seedling.

20. The method as claimed in claim 17 in which the explant is obtained by:
  a) sterilizing cotton seed in a first sterilizing solution;
  b) rinsing the seed with sterile water;
  c) sterilizing the seed in a second sterilizing solution;
  d) rinsing the second sterilization solution from the seed with water;
  e) transferring the sterilized seed to a seed germination medium;
  f) culturing the seed in the seed germination medium in the dark for a period of time sufficient to form a cotton seedling; and
  g) excising the explant from the cotton seedling.

21. The method of claim 20 in which the first sterilizing solution is an aqueous solution containing about 95% by volume ethanol; and the second sterilizing solution is an aqueous solution containing about 15% by weight sodium hypochlorite.

22. A method as claimed in claim 16 in which seed germination medium is a basal agar medium and growth of the seedling is for a period of up to about 14 days prior to excising the explant from the seedling.

23. A method as claimed in claim 16 in which clumps greater than about 800 microns are removed from suspension for plant growth.

24. A method as claimed in claim 16 in which the light intensity during the hours of light is about 3,000 to about 4,000 lux.

25. A method as claimed in claim 16 further including the step of transferring the plantlets from the plant germination medium to soil under conditions of high humidity for a time sufficient to allow the plantlets to mature to a stage sufficient to enable them to be transferred to a hot house and, after said further growth in the hot house, said matured plants are transferred to a field for growth to final maturity.

26. A method as claimed in claim 16 in which the embryogenic clumps less than 800 microns are resuspended in fresh second callus growth medium as per step d) and steps e) and f) are repeated.

27. A method as claimed in claim 16 in which the first callus growth medium is a Murashige and Skoog growth medium containing about 0.4 mg/l thiamine hydrochloride, about 30 g/l glucose, about 2 mg/l naphthaleneacetic acid, about 1 mg/l kinetin and about 100 mg/l inositol.

28. A method as claimed in claim 16 in which the second callus growth medium comprises sucrose and from 1 to about 5 mg/l naphthaleneacetic acid and from 0 to about 1 mg/l cytokinin.

29. A method as claimed in claim 26 in which the liquid callus growth medium contains from 1 to about 5 mg/l naphthaleneacetic acid and from 0 to about 1 mg/l cytokinin.

30. A method as claimed in claim 17 in which the liquid callus growth medium contains from 1 to about 5 mg/l naphthaleneacetic acid and from 0 to about 1 mg/l cytokinin.

31. The method as claimed in claim 15, in which the explant is from a cotton seedling developed by:
   (a) sterilizing cotton seed in a first sterilizing solution;
   (b) rinsing the seed in sterile water;
   (c) sterilizing the seed in a second sterilizing solution;
   (d) rinsing the second sterilization solution from the seed with sterile water;
   (e) transferring the seed to a seed germination medium; and
   (f) growing the seed in the seed germination medium in the dark for a period of time sufficient to produce a seedling; and
   (g) excising the explant from the seedling.

32. The method as defined in claim 31 in which the first sterilizing solution is an aqueous solution containing about 95% by volume ethanol and the second sterilizing solution is an aqueous solution containing about 15% by weight sodium hypochlorite.

33. A method as claimed in claim 31 in which the seed germination medium is a basal agar medium and growth of the seedling in the basal agar medium prior to excising the explant is up to about 4 weeks.

34. A method as claimed in claim 15 in which the light intensity during the hours of light is about 3,000 to about 4,000 lux.

35. The method as claimed in claim 15 further including the step of transferring the plantlet to soil under conditions of high humidity for a time sufficient for the plantlet to mature to a stage sufficient to enable its transfer to a hot house or field for growth to final maturity.

36. A method as claimed in claim 15 in which the first callus growth medium is changed about every ten days while phenolics are secreted from the explant, and thereafter including sucrose in the second solid callus growth medium as the primary carbon source.

37. A method as claimed in claim 16 in which the first callus growth medium is changed about every ten days while phenolics are secreted from the explant, and thereafter including sucrose in the second solid callus growth medium as the primary carbon source.

38. A method for the regeneration of cotton plants from somatic cells of Acala cotton, said method comprising the steps of:
   (a) sterilizing at least one Acala cotton seed in a solution containing 95% by volume ethanol for a period of approximately 2 to 3 minutes;
   (b) rinsing the seed in sterile water;
   (c) soaking the seed in a solution of sodium hypochlorite containing about 15% by weight sodium hypochlorite for a period of from about 15 to about 20 minutes;
   (d) rinsing the seed in sterile water;
   (e) germinating the seed in a dark environment on modified basal agar medium selected from the group consisting of White's medium and half strength Murashige and Skoog medium for a period up to about 14 days to produce a seedling;
   (f) excising at least one segment selected from the group consisting of hypocotyl, cotyledon or mixtures thereof from the seedling;
   (g) culturing the excised segment on first solid callus growth medium which is a Murashige and Skoog medium supplemented with about 0.4 mg/l thiamine hydrochloride, about 30 g/l glucose, about 2 mg/l naphthaleneacetic acid, about 1 mg/l kinetin and about 100 mg/l inositol in an environment of a temperature of from 25° to 30° C. under a light-dark cycle of 16 hours of light followed by about 8 hours of darkness, at about 3,000 to 4,000 lux light intensity during the hours of light during which the medium is replaced by fresh first solid callus growth medium about every 10 days, said light-dark cycle with changes of the medium being repeated until phenolic secretions from the excised segment end, to enable formation of undifferentiated callus from the explant;
   (h) transferring the callus onto Murashige and Skoog medium comprising sucrose and about 2 mg/l naphthaleneacetic acid and about 1 mg/l cytokinetin;
   (i) culturing the callus over a period of about 3 to 4 months to produce at least one embryo;
   (j) transferring the embryo to Beasley and Ting's medium comprising up to about 500 mg/l casein hydrolysate, and containing up to about 1200 mg/l ammonium nitrate and culturing the embryo for a period of about 2 to about 3 months, to produce a plantlet; and
   (k) transferring the plantlet to soil and incubating the plantlet in high humidity to form a plant.

39. The method as defined in claim 38 including the steps of self-pollinating the plant formed from the plantlet to produce seeds and germinating the seeds to produce seedlings.

40. The method of claim 17 in which the first sterilizing solution is an aqueous solution containing about 95% by volume ethanol; and the second sterilizing solution is an aqueous solution containing about 15% by weight sodium hypochlorite.

41. A method as claimed in claim 17 in which seed germination medium is a basal agar medium and growth of the seedling is for a period of up to about 14 days prior to excising the explant from the seedling.

42. A method as claimed in claim 17 in which the light intensity during the hours of light is about 3,000 to about 4,000 lux.

43. A method as claimed ion claim 17 further including the step of transferring the plantlets from the plant germination medium to soil under conditions of high humidity for a time sufficient to allow the plantlets to mature to a stage sufficient to enable them to be transferred to a hot house and, after said further growth in the hot house, said matured plants are transferred to a field for growth to final maturity.

44. A method as claimed in claim 17 in which the embryogenic clumps less than 600 microns are re-suspended in fresh second callus growth medium as per step (d) and steps (e) and (f) are repeated.

45. A method as claimed in claim 17 in which the second callus growth medium comprises sucrose and from 1 to about 5 mg/l naphthaleneacetic acid and from 0 to about 1 mg/l cytokinetin.

46. A method as claimed in claim 17 in which the liquid callus growth medium contains from 1 to about 5 mg/l naphthaleneacetic acid and from 0 to about 1 mg/l cytokinetin.

47. A method as claimed in claim 44 in which the liquid callus growth medium contains from 1 to about 5 mg/l naphthaleneacetic acid and from 0 to about 1 mg/l cytokinetin.

48. A method as claimed in claim 38 in which the first callus growth medium is changed about every 10 days while phenolics are secreted from the explant, and thereafter including sucrose in the second solid callus growth medium as the primary carbon source.

* * * * *

UNITED STATES PATENT AND TRADEMARK OFFICE
CERTIFICATE OF CORRECTION

PATENT NO. : 5,244,802             Page 1 of 6
DATED : September 14, 1993
INVENTOR(S) : Thirumale S. Rangan It is certified that error appears in the above-indentified patent and that said Letters Patent is hereby corrected as shown below:

On the Front Page:

[56] References Cited, OTHER PUBLICATIONS, line 13, change "Rangan eta l." to -- Rangan et al. --.

[56] References Cited, OTHER PUBLICATIONS, line 28, change "palnts." to -- plants. --.

Abstract, line 4, change "This also" to -- These cultures --.

Column 1, line 52, change "Am. Bot." to -- Am. J. Bot. --.

Column 2, line 12, change "2-chlorethyl" to -- 2-chloroethyl --.

Column 2, line 28, after "reference" delete the closing parentheses and insert a comma.

Column 2, line 33, change "barbadense, "" to -- barbadense," --.

Column 2, line 39, after "vitro" delete the period and insert a comma therefor.

Column 4, line 5, change "antibotics" to -- antibiotics --.

Column 5, line 10, before "35Sbt" delete the repetitive slash.

Column 5, line 50, change "SO4" to -- $SO_4$ --.

UNITED STATES PATENT AND TRADEMARK OFFICE
CERTIFICATE OF CORRECTION

PATENT NO. : 5,244,802
DATED : September 14, 1993
INVENTOR(S) : Thirumale S. Rangan It is certified that error appears in the above-indentified patent and that said Letters Patent is hereby corrected as shown below:

Column 6, line 50, change "O4" to -- $O_4$ --.

Column 7, line 5, change "uM" to -- $\mu M$ --.
Column 7, line 53, after "embryos" delete "may".

Column 8, line 31, change "about, 30 g/l" to
    -- about 30 g/l --.
Column 8, line 54, after "culture" delete ", for".
Column 8, line 65, after "during" insert -- the --.
Column 8, line 66, change "secretion" to
    -- secretions --.

Column 9, line 12, change "Other" to -- Others --.
Column 9, line 64, change "as" to -- is --.

Column 10, line 7, after "microns," insert -- and --.
Column 10, line 16, after "Long" insert -- or Erlenmeyer
    flask, containing the liquid embryo growth --.
Column 10, line 49, before "MS" change "a" to -- an --.

Column 11, line 11, change "Aqrobacterium" to
    -- Agrobacterium --.
Column 11, line 34, after "prior" insert -- to --.
Column 11, line 55, after "11" insert a period.

Column 13, line 7, before "actively" change
    "or" to -- of --.
Column 13, line 36, change "field grown plants" to
    -- grown in the field --.
Column 13, line 45, change "stroked/minute" to
    -- strokes/minute --.

UNITED STATES PATENT AND TRADEMARK OFFICE
CERTIFICATE OF CORRECTION

PATENT NO. : 5,244,802

DATED : September 14, 1993

INVENTOR(S) : Thirumale S. Rangan

It is certified that error appears in the above-indentified patent and that said Letters Patent is hereby corrected as shown below:

Column 14, line 28, change "pAL44u4" to -- pAL4404 --.
Column 14, lines 61,64, change "ug" to -- µg -- (both occurrences).

Column 15, lines 19,23, change "ug" to -- µg -- (all occurrences).
Column 15, line 27, after "apparent" change "in" to -- on --.
Column 15, line 28, after "well" change "is" to -- as --.
Column 15, line 39, change "example" to -- Example --.

Column 16, lines 23,30,58,61, change "ug" to -- µg -- (all occurrences).

Column 17, line 54, change "pABDI" to -- pABD1 --.

Column 18, line 1, change "oligonicleotide" to -- oligonucleotide --.
Column 18, line 2, change "mutagensis" to -- mutagenesis --.
Column 18, line 10, change "incorporate" to -- incorporated --.
Column 18, line 13, change "mutagensis" to -- mutagenesis --.
Column 18, line 18, change "40 ul" to -- 40 µl --.

Column 20, line 27, change "incorporate" to -- incorporated --.

UNITED STATES PATENT AND TRADEMARK OFFICE
CERTIFICATE OF CORRECTION

PATENT NO. : 5,244,802
DATED : September 14, 1993
INVENTOR(S) : Thirumale S. Rangan It is certified that error appears in the above-indentified patent and that said Letters Patent is hereby corrected as shown below:

Column 21, lines 18,19, change "plasmic" to
-- plasmid --.
Column 21, line 25, before "digestion" delete the comma.
Column 21, line 67, change "50ug/ml" to -- 50 µg/ml --.

Column 22, line 9, before "constructed" delete "was".
Column 22, line 28, change "mutagensis" to
-- mutagenesis --.

Column 23, line 5, after "Formula" insert -- 1. --.
Column 23, line 17, change "endonuclese" to
-- endonuclease --.
Column 23, lines 36,37, change "mutagensis" to
-- mutagenesis -- (both occurrences).
Column 23, line 42, after "plasmid," insert -- in --.
Column 23, line 43, change "shown in FIG. 32 is selected for on" to -- as shown in FIG. 32, is selected for --.
Column 23, lines 48,49, change "ug/ml" to -- µg/ml --
(both occurrences).

Column 24, lines 8,9,20,28,29,32, change "ug" and "ul"
(all occurrences) to -- µg -- and -- µl --,
respectively.
Column 24, line 23, change "reference]using" to
-- reference using --.
Column 24, line 26, after "(see below)" delete the
bracket.
Column 24, line 37, after "in" delete the comma.
Column 24, line 51, change "H2O" to -- $H_2O$ --.

UNITED STATES PATENT AND TRADEMARK OFFICE
CERTIFICATE OF CORRECTION

PATENT NO. : 5,244,802
DATED : September 14, 1993
INVENTOR(S) : Thirumale S. Rangan It is certified that error appears in the above-indentified patent and that said Letters Patent is hereby corrected as shown below:

Column 25, line 57, after "cup" delete the period.
Column 25, lines 57,58, change "covered" to -- cover --.

Column 26, lines 39,40, between "Example 17" and before the paragraph beginning on line 40, insert the following heading: -- Cotton Regenerants with altered growth habits --.
Column 26, line 49, change "desireable" to -- desirable --.

Column 28, line 19, change "descried" to -- described --.

Column 29, line 63, under "3270" change "TGTGTACAAG" to -- TGTGTAGAAG --.

Column 32, line 4, under "3950" change "TTTTCTGGAG" to -- TTTTCTGAAG --.

UNITED STATES PATENT AND TRADEMARK OFFICE
CERTIFICATE OF CORRECTION

PATENT NO. : 5,244,802
DATED : September 14, 1993
INVENTOR(S) : Thirumale S. Rangan It is certified that error appears in the above-indentified patent and that said Letters Patent is hereby corrected as shown below:

Column 34, line 17, before "group" insert -- a --.

Column 38, line 64, after "claimed" change "ion" to -- in --.

Signed and Sealed this

Sixth Day of December, 1994

Attest:

BRUCE LEHMAN

Attesting Officer

Commissioner of Patents and Trademarks